United States Patent
Ung et al.

(10) Patent No.: US 12,370,045 B2
(45) Date of Patent: Jul. 29, 2025

(54) METHODS AND SYSTEMS FOR DELIVERY DEVICE INSERTION DURING MEDICAL DEVICE CRIMP PROCESSES

(71) Applicant: MEDTRONIC, INC., Minneapolis, MN (US)

(72) Inventors: Victoria Ung, Santa Rosa, CA (US); James E. Mitchell, Windsor, CA (US); Nathanael J. Glucklich, Santa Rosa, CA (US)

(73) Assignee: Medtronic, Inc., Minneapolis, MN (US)

( * ) Notice: Subject to any disclaimer, the term of this patent is extended or adjusted under 35 U.S.C. 154(b) by 764 days.

(21) Appl. No.: 17/475,519

(22) Filed: Sep. 15, 2021

(65) Prior Publication Data

US 2022/0087818 A1   Mar. 24, 2022

Related U.S. Application Data

(60) Provisional application No. 63/080,343, filed on Sep. 18, 2020.

(51) Int. Cl.
*A61F 2/24*   (2006.01)
(52) U.S. Cl.
CPC ................... *A61F 2/2436* (2013.01)
(58) Field of Classification Search
CPC .... A61F 2/9522; A61F 2/9524; A61F 2/9525; A61F 2/9526
See application file for complete search history.

(56) References Cited

U.S. PATENT DOCUMENTS

| | | | | |
|---|---|---|---|---|
| 5,785,715 A | * | 7/1998 | Schatz | A61B 17/22032 606/1 |
| 5,810,873 A | * | 9/1998 | Morales | A61F 2/9525 606/1 |
| 5,817,100 A | * | 10/1998 | Igaki | A61F 2/97 623/1.11 |
| 6,018,857 A | * | 2/2000 | Duffy | A61F 2/9525 29/516 |
| 6,106,531 A | * | 8/2000 | Schatz | A61F 2/958 606/108 |
| 6,132,458 A | * | 10/2000 | Staehle | A61F 2/95 623/1.11 |
| 8,608,770 B2 | | 12/2013 | Forster et al. | |
| 9,265,607 B2 | | 2/2016 | Glazier | |
| 9,757,232 B2 | | 9/2017 | Peterson et al. | |
| 10,973,631 B2 | | 4/2021 | Scheinblum et al. | |
| 2001/0007082 A1 | * | 7/2001 | Dusbabek | A61F 2/958 623/1.11 |

(Continued)

FOREIGN PATENT DOCUMENTS

WO    2022046319 A1    3/2022

*Primary Examiner* — Shaun L David
(74) *Attorney, Agent, or Firm* — Medler Ferro Woodhouse & Mills PLLC

(57) ABSTRACT

A system for assisting in loading an implantable medical device onto a delivery system includes a body having a first end, a second end, and a conduit extending from the first end to the second end. The body has an inner diameter that allows a distal portion of the delivery system to slidably move through the conduit. The body has an outer diameter that allows the body to be inserted into a central lumen of the implantable medical device.

17 Claims, 32 Drawing Sheets

(56) References Cited

U.S. PATENT DOCUMENTS

| | | | |
|---|---|---|---|
| 2002/0029077 A1* | 3/2002 | Leopold | A61F 2/07 606/108 |
| 2002/0099431 A1* | 7/2002 | Armstrong | A61F 2/958 623/1.11 |
| 2002/0116045 A1* | 8/2002 | Eidenschink | A61F 2/958 606/108 |
| 2003/0083730 A1* | 5/2003 | Stinson | A61F 2/95 623/1.11 |
| 2003/0139795 A1* | 7/2003 | Olson | A61F 2/95 623/1.11 |
| 2007/0239271 A1* | 10/2007 | Nguyen | A61F 2/9525 623/2.11 |
| 2007/0270937 A1* | 11/2007 | Leanna | A61F 2/95 623/1.12 |
| 2007/0288080 A1* | 12/2007 | Maccollum | A61F 2/82 623/1.11 |
| 2009/0182407 A1* | 7/2009 | Leanna | A61F 2/9525 623/1.11 |
| 2009/0299451 A1* | 12/2009 | Ellsworth | A61F 2/82 623/1.11 |
| 2010/0057185 A1* | 3/2010 | Melsheimer | A61F 2/9525 623/1.11 |
| 2011/0295216 A1* | 12/2011 | Miller | A61F 2/95 604/264 |
| 2012/0330408 A1* | 12/2012 | Hillukka | A61F 2/2427 623/2.11 |
| 2013/0218266 A1* | 8/2013 | Chalekian | A61F 2/958 623/2.11 |
| 2018/0071092 A1* | 3/2018 | Faurie | A61B 17/3468 |
| 2018/0236205 A1* | 8/2018 | Krautkremer | A61M 25/0668 |

* cited by examiner

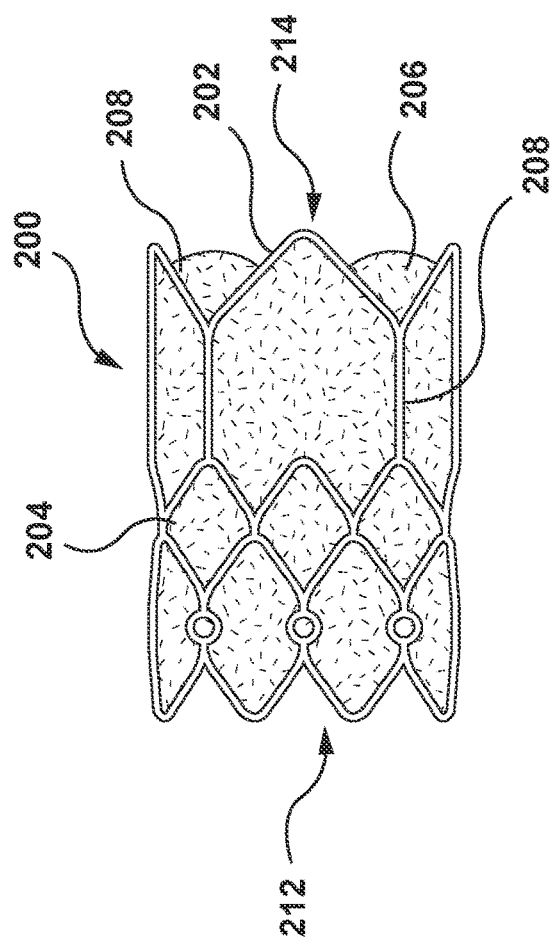
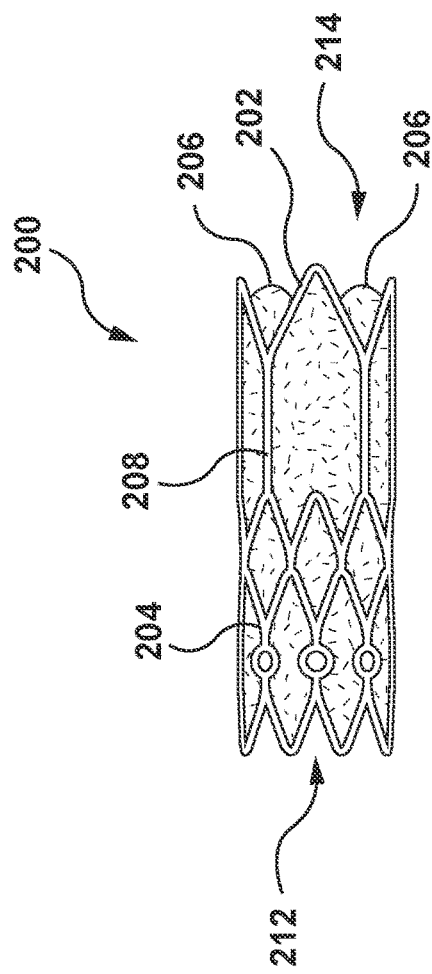
FIG. 2A
FIG. 2B

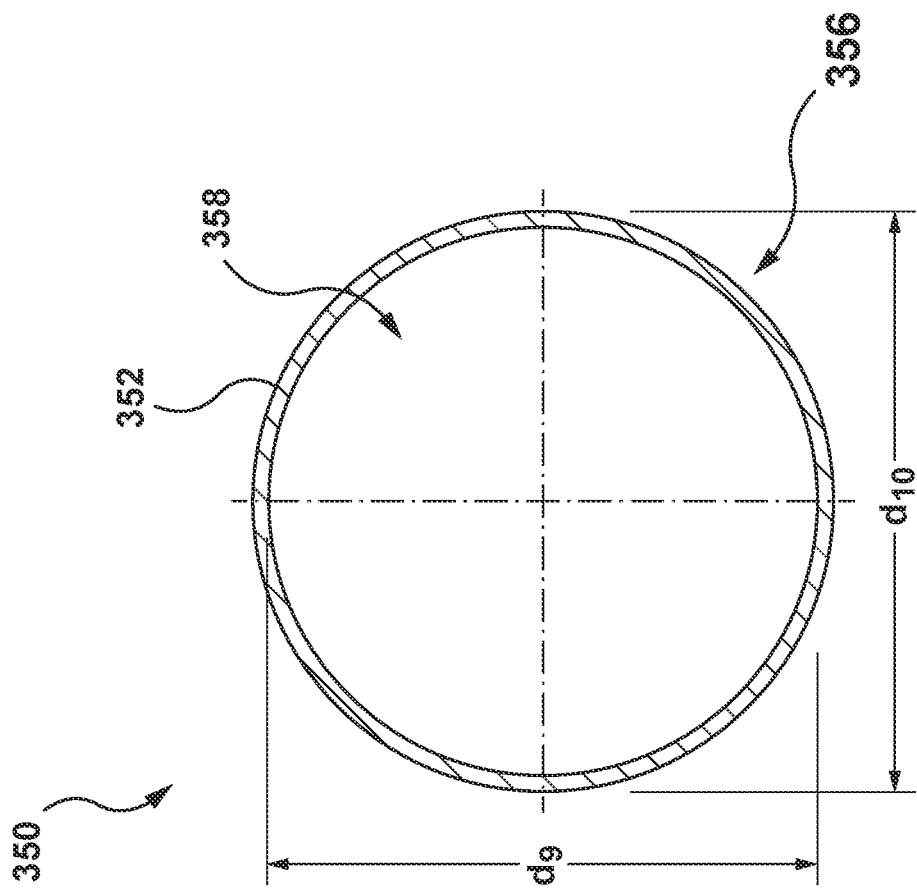
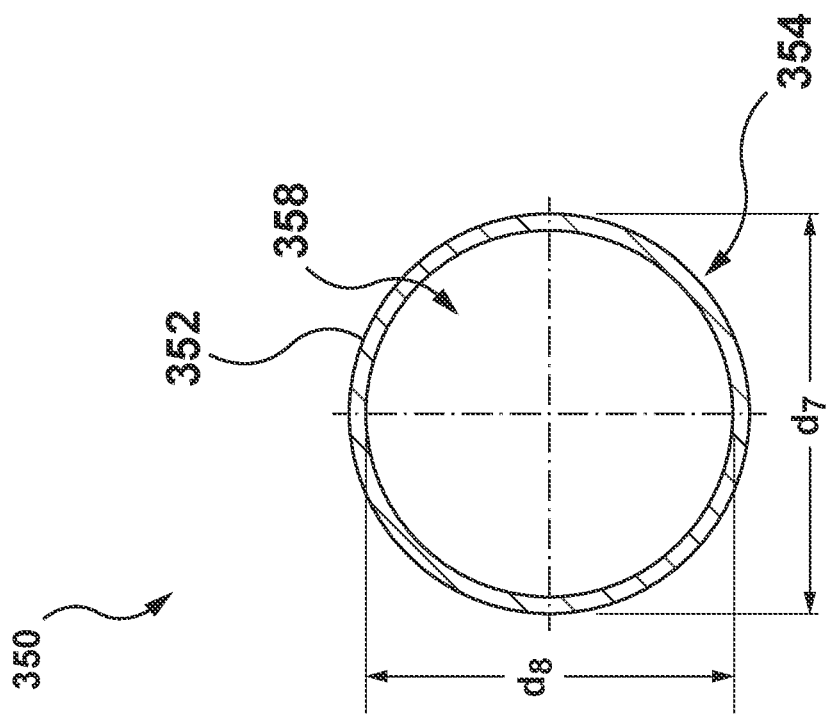

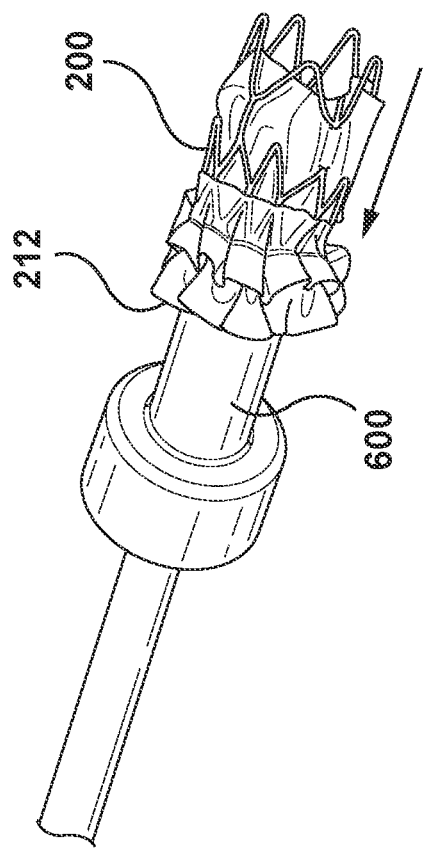
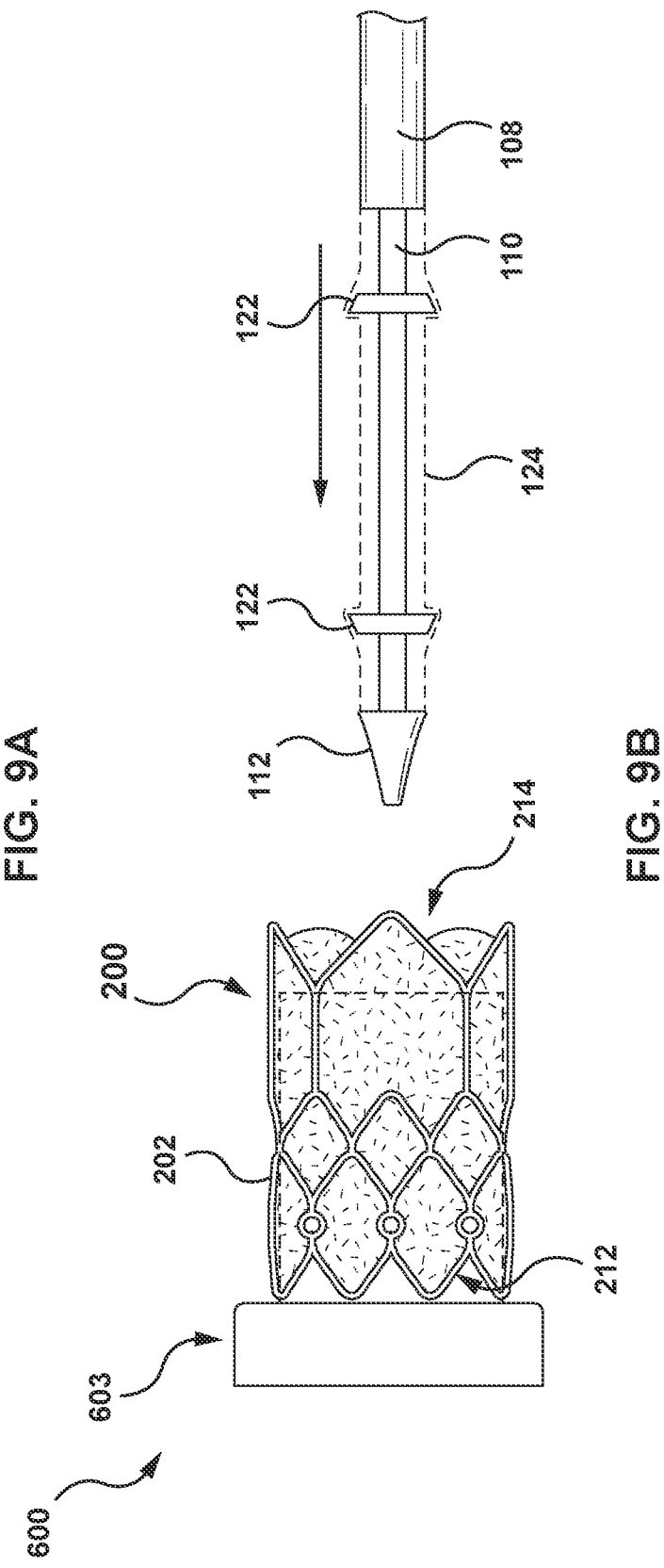

METHODS AND SYSTEMS FOR DELIVERY DEVICE INSERTION DURING MEDICAL DEVICE CRIMP PROCESSES

CROSS-REFERENCE TO RELATED APPLICATIONS

The present application claims the benefit under 35 U.S.C. § 119 of U.S. Provisional Application No. 63/080,343, filed Sep. 18, 2020, the contents of which are incorporated by reference herein in their entirety.

FIELD

The present technology is generally related to medical devices. And, more particularly, to systems and methods for loading stents, prosthetic heart valves and other implantable medical devices onto delivery systems.

BACKGROUND

Patients suffering from various medical conditions or diseases may require surgery to install an implantable medical device. For example, valve regurgitation or stenotic calcification of leaflets of a heart valve may be treated with a prosthetic heart valve. A traditional surgical procedure to implant the prosthetic heart valve requires a sternotomy and a cardiopulmonary bypass, which creates significant patient trauma and discomfort. Traditional surgical procedures may also require extensive recuperation times and may result in life-threatening complications.

One alternative to a traditional surgical procedure is delivering implantable medical devices using minimally-invasive techniques. For example, a prosthetic heart valve can be percutaneously and transluminally delivered to an implant location. In such methods, the prosthetic heart valve can be compressed or crimped on a delivery catheter for insertion within a patient's vasculature; advanced to the implant location; and re-expanded to be deployed at the implant location. In this example, a catheter loaded with the prosthetic heart valve in a compressed state can be introduced through an opening in a blood vessel, for example, the femoral artery, aortic artery, or the subclavian artery, and advanced to the heart. At the heart, the prosthetic heart valve can be re-expanded to be deployed at the implant location, e.g., the aortic valve annulus.

In one minimally-invasive technique, an implantable medical device such as a prosthetic heart valve may be delivered using a balloon catheter for the delivery catheter/system with the prosthetic heart valve including a valve structure installed in a balloon expandable frame or stent. In this approach, a crimper may to compress and load the transcatheter valve device onto the balloon catheter. For example, the crimper operates to radially compress the implantable medical device until it is in direct contact with the delivery system. The crimper may also aid in the correct positioning of the implantable medical device when compressing it onto the delivery system in order to prevent damage to the implantable medical device, delivery system, or both.

In operation, the crimper needs to be able to open large enough to allow placement of the implantable medical device inside a crimper chamber in order to radially compress the implant onto the delivery system by a controlled reduction of the volume of the crimper chamber. The crimper also needs to be capable of reducing the crimper chamber in size to be small enough during the radial compression for the implant to be adequately crimped to the delivery system. To accommodate this, the implantable medical device may be reduced in diameter prior to insertion into the crimper, e.g., partially compressed. When partially compressed, insertion of the delivery system into the partially crimped implantable medical device during the crimp process can pose a risk of damaging the implantable medical device or delivery system. Depending on the design of the implantable medical device and the diameter in the partially compressed state, a risk of damaging the implantable medical device may increase due to crowding and packing of the components of the implantable medical device, e.g., crowding and packing of leaflet material within the inner diameter of the stent or frame of the prosthetic heart valve.

SUMMARY

The techniques of this disclosure generally relate to guide systems for assisting with the loading an implantable medical device onto a delivery device.

In one aspect, the present disclosure provides a system for assisting in loading an implantable medical device onto a delivery system. The system includes a body having a first end, a second end, and a conduit extending from the first end to the second end. The body has an inner diameter that allows a distal portion of the delivery system to slidably move through the conduit. The body has an outer diameter that allows the body to be inserted into a central lumen of the implantable medical device.

In another aspect, the present disclosure provides a system for assisting in loading an implantable medical device onto a delivery system. The system includes a base having a first base end, a second base end, and a base conduit extending from the first end to the second end. The system also includes a body having a first body end, a second body end, and a body conduit extending from the first end to the second end. The second body end is coupled to the first base end to define a guide conduit comprising the base conduit and the body conduit. The guide conduit has a diameter that allows a distal portion of the delivery system to slidably move through the guide conduit. The body has an outer diameter that allows the body to be inserted into a central lumen of the implantable medical device.

In another aspect, the present disclosure provides a method for loading a prosthetic heart valve onto a delivery system. The method includes inserting a guide system into a central lumen of the prosthetic heart valve. The guide system includes a body that defines a conduit within an interior of the body. The method also includes inserting a distal portion of the delivery system into the conduit of the guide system. Further, the method includes aligning one or more retention members of the distal portion of the delivery system with the prosthetic heart valve. Additionally, the method includes removing the guide system from the central lumen of the prosthetic heart valve. The method includes compressing the prosthetic heart valve onto the distal portion of the delivery device.

The details of one or more aspects of the disclosure are set forth in the accompanying drawings and the description below. Other features, objects, and advantages of the techniques described in this disclosure will be apparent from the description and drawings, and from the claims.

BRIEF DESCRIPTION OF DRAWINGS

The foregoing and other features and advantages of the present disclosure will be apparent from the following description of embodiments hereof as illustrated in the accompanying drawings. The accompanying drawings, which are incorporated herein and form a part of the specification, further serve to explain the principles of the present disclosure and to enable a person skilled in the pertinent art to make and use the embodiments of the present disclosure. The drawings are not to scale.

FIGS. 2A-2D depict an illustration of a prosthetic heart valve that may be used with the guide systems, according to an embodiment hereof.

FIGS. 3A-3I depict several illustrations of a guide system for use with an implantable medical device, according to an embodiment hereof

FIG. 8, FIGS. 9A-9C, and FIGS. 10A-10C depict an operation of the guide systems of FIGS. 6A-6H and FIGS. 7A-7G, according to an embodiment hereof.

DETAILED DESCRIPTION

Figure 1A:
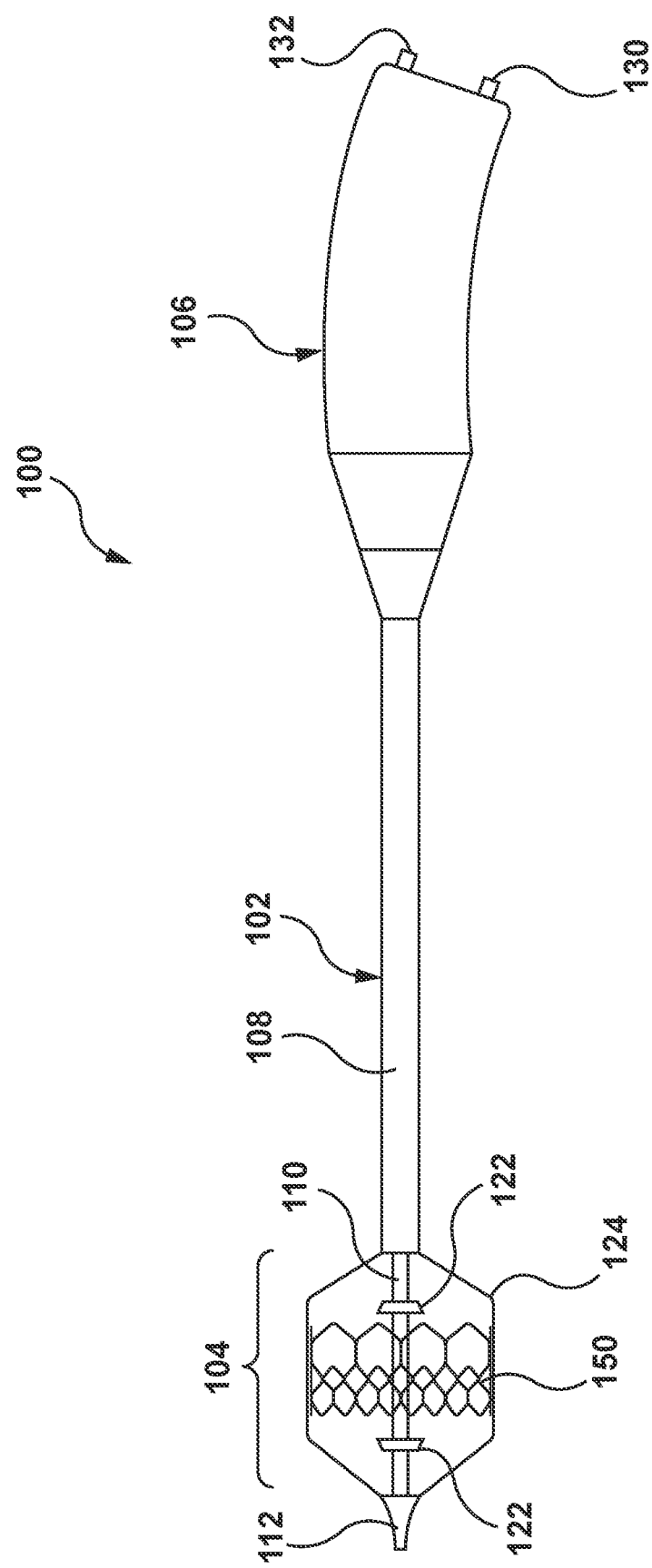
FIGS. 1A and 1B depict an illustration of a delivery system that may be used with guide systems, according to an embodiment hereof.

Specific embodiments of the present disclosure are now described with reference to the figures. The following detailed description describes examples of embodiments and is not intended to limit the present technology or the application and uses of the present technology. Although the description of embodiments hereof is in the context of a guide system that may be used in loading an implantable medical device onto a delivery system, the present technology may also be used in other devices. Furthermore, there is no intention to be bound by any expressed or implied theory presented in the preceding technical field, background, brief summary or the following detailed description.

The terms "distal" and "proximal", when used in the following description to refer to a delivery system or catheter are with respect to a position or direction relative to the treating clinician. Thus, "distal" and "distally" refer to positions distant from, or in a direction away from the treating clinician, and the terms "proximal" and "proximally" refer to positions near, or in a direction toward the clinician.

Embodiments disclosed herein are directed to guide systems for assisting with the loading and compressing an implantable medical device onto a delivery device. The process of compressing an implant to a delivery system involves a step to insert a distal portion of the delivery system into the implantable medical device. The insertion step can damage the implantable medical device if the distal portion of the delivery system contacts components of the implantable medical device. For example, if the distal portion of the delivery system contacts a valve structure, e.g., leaflets, of a prosthetic heart valve, the contact can lead to tears or punctures. The contact may also cause the leaflets to be inverted when the delivery system is inserted through one end, e.g., an outflow end, of the prosthetic heart valve. This probability of damage may increase if the implantable medical device has a small diameter, is partially crimped, or is designed such that the leaflets are in a closed position in the unloaded stated.

In embodiments, a guide system operates to mitigate potential damage from inserting a distal portion of a delivery system into an implantable medical device during compression and loading processes. The guide system provides a conduit for the delivery system as well as protects components of the implantable medical device, e.g., leaflets, stent, etc., from damage by the delivery system. The guide system includes one or more structures that form a conduit through which a distal portion of the delivery system may be inserted. The guide system is inserted into the implantable medical device before inserting the delivery system into the implantable medical device. As the distal portion of the delivery system is inserted, the guide system operates as a buffer between the distal portion of the delivery system and the implantable medical device. Additionally, the guide system operates to orient components of the implantable medical device. For example, the guide system can position leaflets of a prosthetic heart valve from a closed position to an open position and prevent the inversion of the leaflets during the insertion of the delivery system.

Figure 1B:
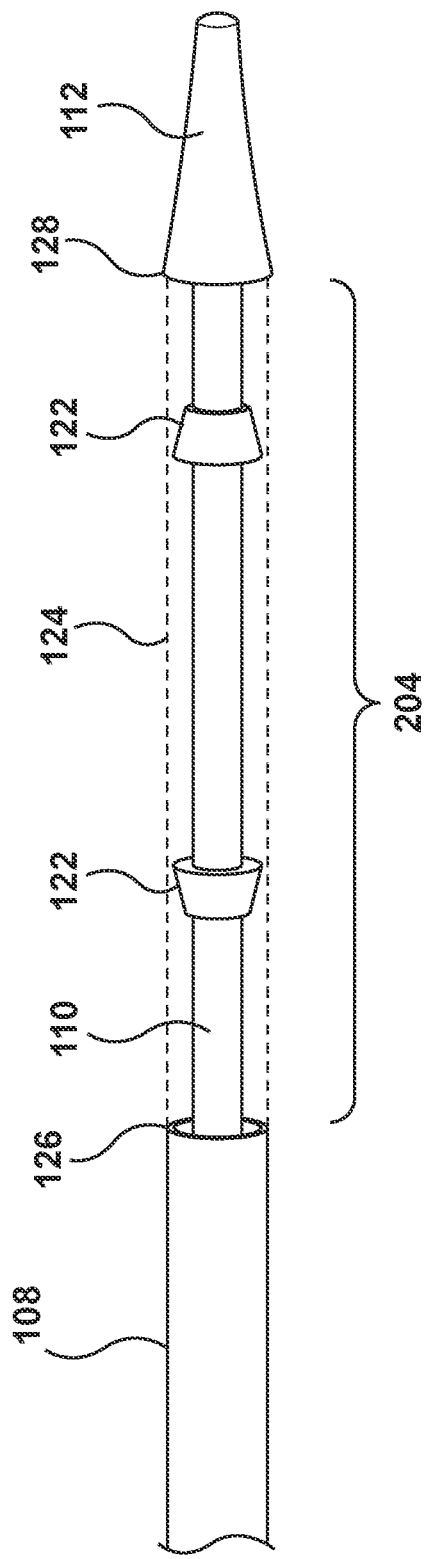

In embodiments described herein, the guide systems are configured to operate in combination with a delivery system to load a prosthetic heart valve onto a portion of the delivery system. FIGS. 1A and 1B illustrate an example of a delivery system 100 in accordance with an embodiment hereof. One skilled in the art will realize that FIGS. 1A and 1B illustrate one example of a delivery system and that existing components illustrated in FIGS. 1A and 1B may be removed and/or additional components may be added to the delivery system 100.

As shown in FIG. 1A, delivery system 100 generally comprises a catheter portion 102 having a distal portion 104. The catheter portion 102 is coupled to a proximal handle portion 106 by which the catheter portion 102 is manipulated and through inflation fluid is delivered to an expansion device (balloon) 124 (illustrated in an expanded state) located at the distal portion 104. A nosecone 112 is coupled to a distal end of the distal portion 104 as the leading feature of delivery system 100. The catheter portion 102 is preferably of a length and size so as to permit a controlled delivery of the distal portion 104 to a desired implant location, for example, a patient's heart. In embodiments, the catheter portion 102 includes features to enhance maneuverability, steerability and advancement of the distal portion 104 to the point of implantation. The distal portion 104 provides the means by which an implantable medical device 150, e.g., a prosthetic valve structure and stent, (illustrated in an expended state) can be mounted for delivery to the implant location and further provides for allowing the expansion of the implantable medical device 150 for effective deployment thereof. The control handle portion 106 preferably controls movements as translated to the distal portion 104 by way of elongate structure of the catheter portion 102. Controlled functionality from the control handle portion 106 is preferably provided in order to permit expansion and deployment of the implantable medical device 150 at a desired location, such as a heart valve annulus, and to provide for ease in the delivery and withdrawal of the delivery system through a patient's vasculature.

The catheter portion 102 of the delivery system 100 also preferably comprises an outer shaft 108 that is also operatively connected with a distal end of the control handle portion 106 and that surrounds one or more inner shafts, such as an inner shaft 110, over at least a part of its length.

In embodiments, the outer shaft 108 comprises a lubricous inner layer (such as high density polyethylene HDPE or Polytetrafluoroethylene PTFE), braided stainless steel middle layer with a flexible plastic outer layer, such as comprised of Pebax 7233, or Nylon 12. The outer shaft 108 extends from the control handle portion 106 and facilitates the advancement and steering of the delivery system along a guide wire and through a patient's vasculature by improving the pushability of the delivery system 100.

The inner shaft 110 is operatively connected with the control handle portion 106 so as to be movable by operation of the control handle portion 106. As illustrated in FIG. 1B, which is an enlarged view of the distal portion 104 with the implantable medical device 150 removed and the expansion device 124 in an unexpanded state (deflated), one or more retention members (or bumpers) 122 are coupled to the inner shaft 110. The retention members 122 are configured to retain or hold the implantable medical device 150 in position on the expansion device 124, once the implantable medical device 150 is compressed onto the expansion device 124. In some embodiments, as illustrated below in FIG. 1B, the retention members 122 can be trapezoidal shaped bumpers that extend around the circumference of the inner shaft 110. In embodiments, the expansion device 124 can be an inflatable balloon that can be used to expand the implantable medical device 150 once positioned at an implantation location within a patient. The retention members 122 can prevent migration of the implantable medical device off the expansion device 124 by operating as physical barriers.

In embodiments, the expansion device 104 can be coupled to the outer shaft 108 at a proximal end 126 of the expansion device 104, thereby placing an interior of the expansion device in fluid communication with a lumen formed between the outer shaft 108 and the inner shaft 110. The expansion device 104 can also be coupled to the nosecone 112 at a distal end 128 of the expansion device. The expansion device 124 can be activated by the control handle portion 106 in order to expand the implantable medical device. For example, the expansion device 124 can be activated by introducing a gas or liquid into the lumen between the outer shaft 108 and the inner shaft 110 via an inflation port 130 illustrated in FIG. 1A, which is communicated to the interior of the expansion device 124.

As illustrated in FIGS. 1A and 1B, the catheter portion 102 can include other components for operation of the delivery system. In some embodiments, the inner shaft 110 can also include an axial lumen (not shown) extending entirely through at least the inner shaft 110, the purpose of which is for receiving a guidewire in order for the delivery system 100 to be guided along a patient's vasculature to an implant location. The guidewire can be introduced to the axial lumen via a guidewire port 132 located on the control handle portion 106. The guidewire, not shown, may be used in a conventional manner to guide the delivery system along it and with its distal end guided to its desired implant location.

Figure 2D:
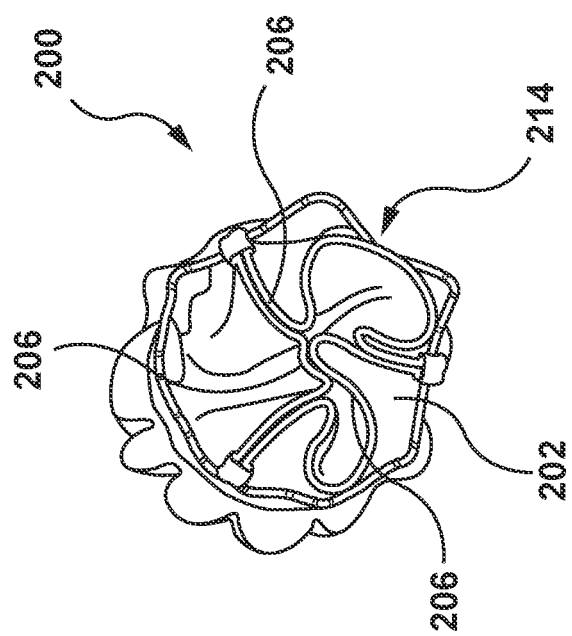

A non-limiting example of an implantable medical device 150 useful with systems, devices and methods of the present disclosure is illustrated in FIGS. 2A-2D. In particular, FIG. 2A illustrates a side view of a prosthetic heart valve 200 in a normal or expanded (uncompressed) state. FIG. 2B illustrates the prosthetic heart valve 200 in a compressed state (e.g., when compressively retained on a delivery system such as the distal portion 104 of the delivery system 100). The prosthetic heart valve 200 includes a stent or frame 202 and a valve structure 204. The stent 202 can assume any of the forms, and is generally constructed so as to be expandable from the compressed state (FIG. 2B) to the uncompressed state (FIG. 2A). In other embodiments, the stent 202 is designed to be expanded to the uncompressed state by a separate device (e.g., the expansion device 124 internally located within the stent 202). In some embodiments, the stent 202 is self-expanding. The valve structure 204 is coupled to the stent 202 and provides two or more (typically three) leaflets 206. The valve structure 204 can be coupled to the stent 202 in various manners, such as by sewing the valve structure 204 to one or more of the wire segments or commissure posts defined by the stent 202.

In embodiments, the prosthetic heart valve 200 of FIGS. 2A and 2B can be configured to replace or repair an aortic valve. Alternatively, other shapes are also envisioned, adapted to the specific anatomy of the valve to be repaired (e.g., prosthetic heart valves in accordance with the present disclosure can be shaped and/or sized for replacing a native mitral, pulmonic, or tricuspid valve). With the example of FIGS. 2A and 2B, the valve structure 204 extends less than the entire length of the stent 202, but in other embodiments the valve structure can extend along an entirety, or a near entirety, of a length of the stent 202. A wide variety of other constructions are also acceptable and within the scope of the present disclosure.

The stent 202 includes support structures that comprise a number of struts or wire portions 308 arranged relative to each other to provide a desired compressibility and strength to the valve structure 204. While not illustrated, the stent 202 can also include one or more attachment members that removably couple the prosthetic heart valve 200 to a delivery system, e.g., the delivery system 100. One skilled in the art will realize that the attachment members can be any type of device such as paddles, eyelets, loops, slots, or any other suitable coupling member. The stent 202 can include one or more radiopaque markers that aid in the positioning and orientation of the prosthetic heart valve 200.

Figure 2C:
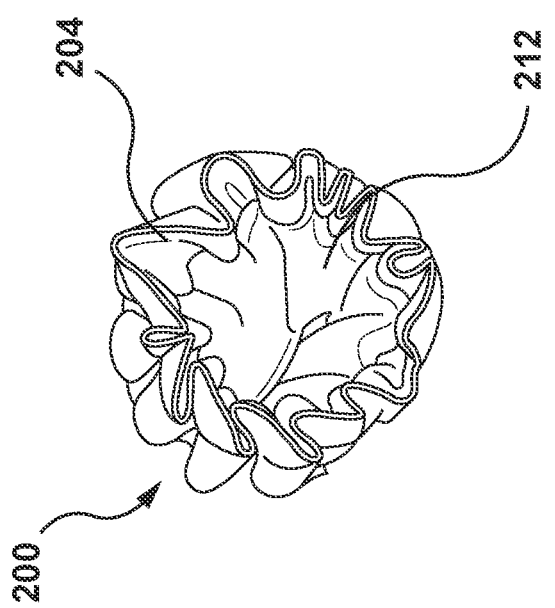

The struts or wire portions 208 form a central lumen having an inflow end 212 and an outflow end 214, as further illustrated in FIGS. 2C and 2D, which are views of the inflow end 212 and the outflow end 214, respectively. As illustrated in FIGS. 2C and 2D, the stent 202 can generally be a tubular support structure defining the central lumen in which the valve structure 204 can be secured. As illustrated in FIG. 2D, the leaflets 206 can be oriented proximal to the outflow end 214. The leaflets 206 can be formed from a variety of materials, such as autologous tissue, xenograph material, or synthetics as are known in the art. In some embodiments, the leaflets 206 may be provided as a homogenous, biological valve structure, such as porcine, bovine, or equine valves. In some embodiments, the leaflets 206 can be provided independent of one another and subsequently assembled to the support structure of the stent 202. In some embodiments, the stent 202 and the leaflets 206 can be fabricated at the same time. The stent 202 can be configured to accommodate at least two (typically three) leaflets 206 but can incorporate more or fewer than three leaflets 206.

The struts or wire portions 208 can be arranged such that the struts or wire portions 308 are capable of transitioning from the compressed state to the uncompressed state. These wires are arranged in such a way that the stent 202 allows for folding or compressing or crimping to the compressed state in which the internal diameter is smaller than the internal diameter when in the uncompressed state. In the compressed state, the stent 202 with attached valve structure 204 can be mounted onto a delivery system, such as the distal portion 104 the delivery system 100. The stent 202 is configured so that they can be changed to an uncompressed state when desired by use of the expansion device 124.

In embodiments, the struts or wire portions 308 of the stent 202 can be formed of a metal or other material that can be expanded from a compressed state to an uncompressed state by an expansion device, e.g., balloon. In some embodiments, the wires of the stent 202 can be formed from a shape memory material such as a nickel titanium alloy (e.g., Nitinol) that is self-expandable from the compressed state to the expanded state, such as by the application of heat, energy, and the like, or by the removal of external forces (e.g., compressive forces). The stent 202 can also be compressed and re-expanded multiple times without significantly damaging the structure of the stent frame. In addition, the stent 202 may be laser-cut from a single piece of material or may be assembled from a number of different components or manufactured from a various other methods known in the art.

FIGS. 3A-3I illustrate several examples of a guide system 300 in accordance with an embodiment hereof. One skilled in the art will realize that FIGS. 3A-3I illustrate several examples of a guide system and that existing components illustrated in FIGS. 3A-3I may be removed and/or additional components may be added to the guide system 300.

Figure 3A:
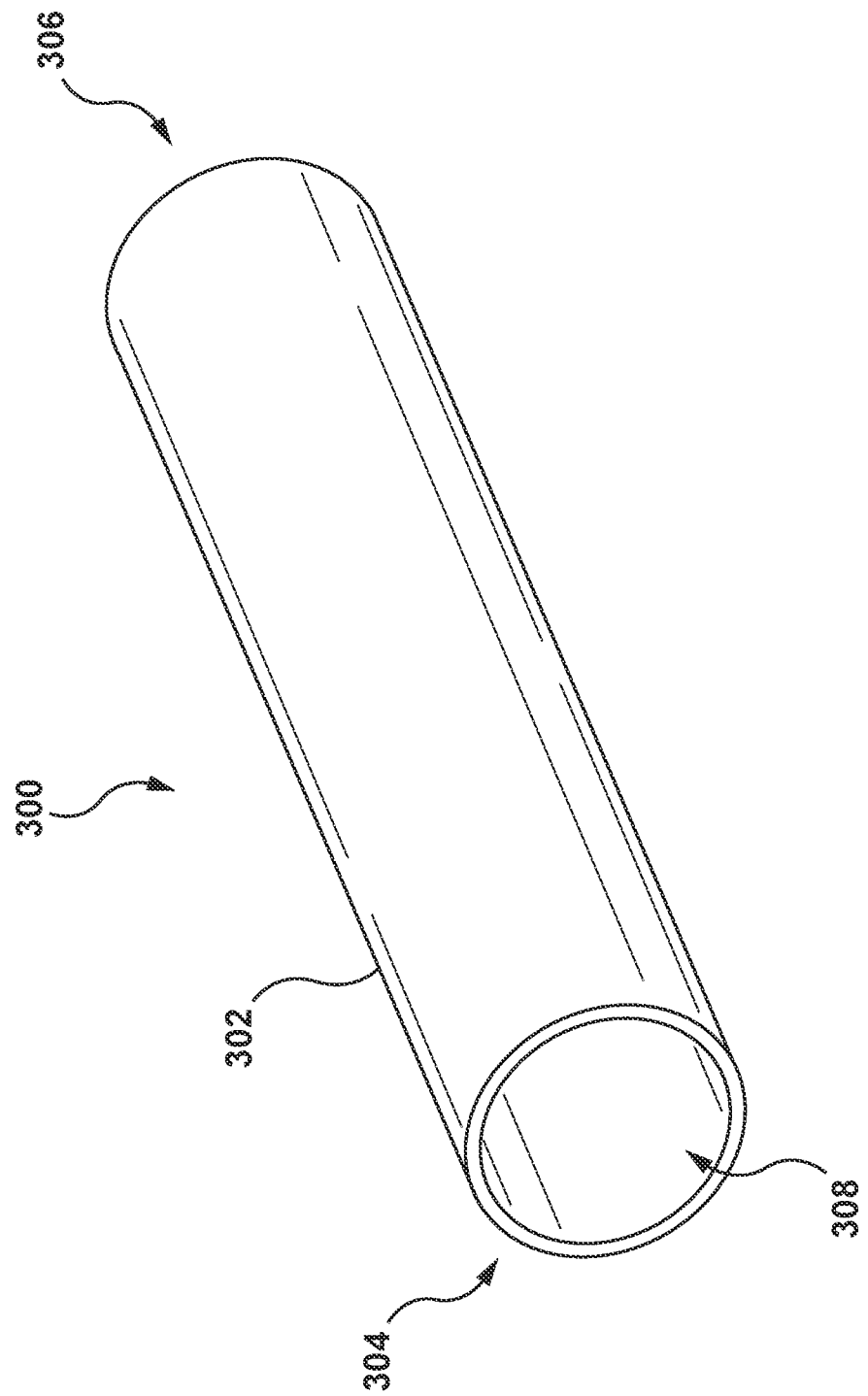

As disclosed herein, the guide system 300 can be utilized on implantable medical devices (e.g., a prosthetic heart valve 200 as described above with reference to FIGS. 2A-2D) that are to be loaded and delivered transluminally via portions of a delivery system (e.g., a delivery system 100 as described above with reference to FIGS. 1A and 1B). As illustrated in FIG. 3A, which is a perspective view, the guide system 300 includes a body 302 with a first end 304 and a second end 306. The body 302 can be formed as a hollow cylindrical tube having a cylindrical shape thereby defining a conduit 308. In operation, the guide system 300 can inserted into the implantable medical device and the conduit 308 provides a pathway for inserting the delivery system. The body 302 of the guide system 300 protects the components of the implantable medical device, e.g., leaflets of a valve structure, from damage by the delivery system when the delivery system inserted into the conduit 308.

Figure 3B:
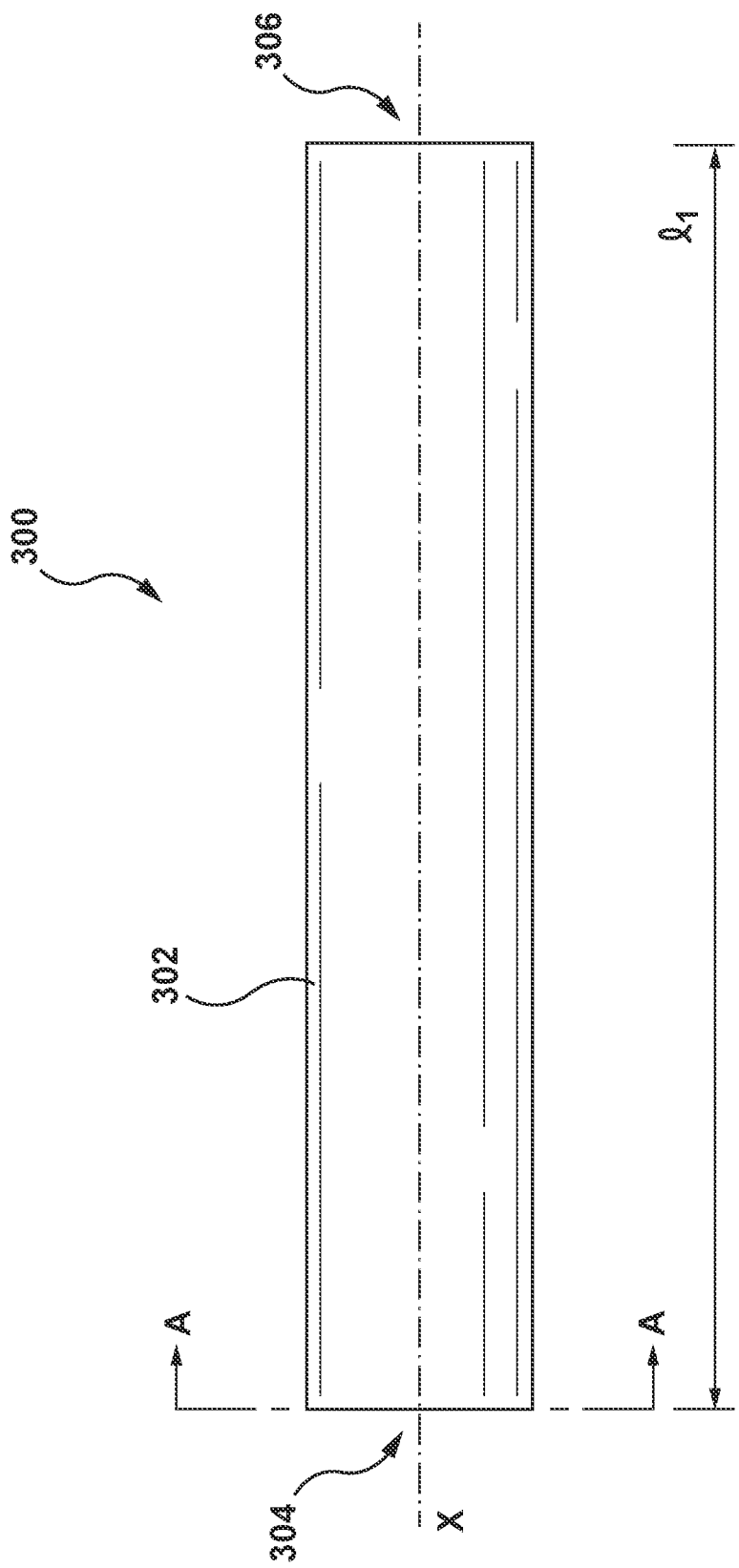

As illustrated in FIG. 3B, which is a side view of the guide system 300, the body 302 can be formed having a length, $l_1$, that is measured along a long axis, x, of the body 302. In embodiments, the length, $l_1$, of the body 302 can be any length that allows the guide system 300 to fit within an implantable medical device and extend beyond the ends of the implantable medical device. For example, the length, $l_1$, of the body 302 can be formed to a length that allows the first end 304 and the second end 306 to extend beyond the ends of the prosthetic heart valve 200 when inserted into the central lumen of the prosthetic heart valve 200 in an uncompressed state. In embodiments, the length, $l_1$, of the body 302 can be based on a size and configuration of the implantable medical device and/or crimp length. For example, the length, $l_1$ of the body 302 can range between approximately 21 millimeters (mm) to approximately 34 mm. One skilled in the art will realize that any examples of dimensions describe herein are approximate values and can vary by, for example, +/−5.0%, based on manufacturing tolerances, operating conditions, and/or other factors.

Figure 3C:
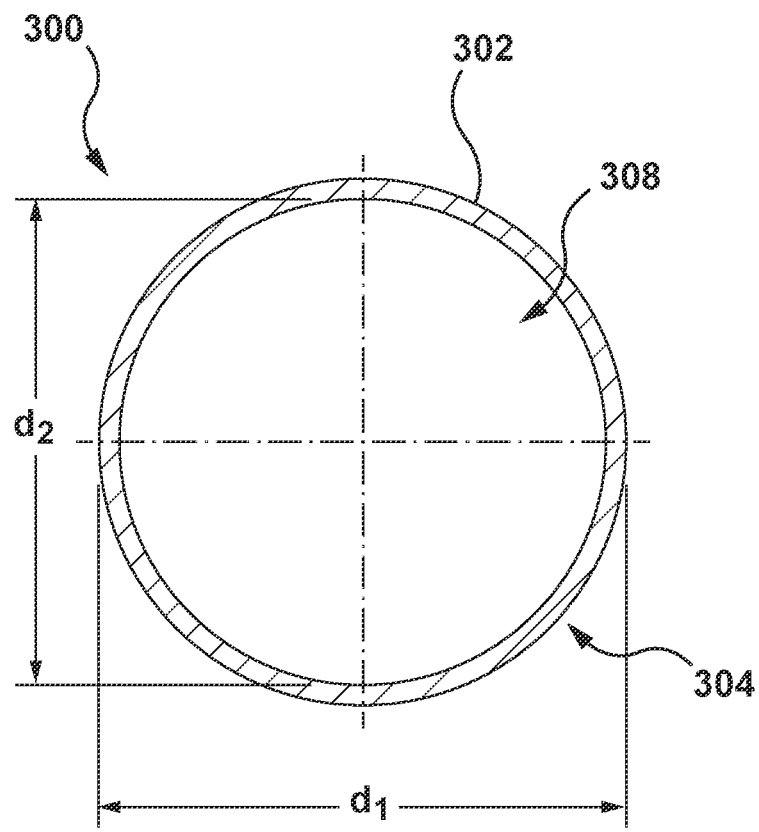

FIG. 3C illustrates a cross-sectional view of the guide system 300 taken along the line A at the first end 304. As illustrated, the guide system 300 is formed in a cylindrical shape having an approximately circular cross-section. The body 302 defines the conduit 308 having an approximate circular cross-section. The body 302 can be formed having an outer diameter, $d_1$, and an inner diameter, $d_2$. As such, the diameter of the conduit 308 can correspond to the inner diameter, $d_2$. In embodiments, the outer diameter, $d_1$, of the body 302 can be any diameter that allows the guide system 300 to fit within an implantable medical device, e.g., allows the body 302 to fit within the central lumen of the prosthetic heart valve 200. Likewise, the inner diameter, $d_2$, can be any diameter that allows a distal portion of the delivery system to be inserted into the conduit 308, e.g., allows the circumference of distal portion 104 of the delivery system 100 including the retention members 122 to fit within the conduit 308. For example, the outer diameter, $d_1$, of the body 302 can range between approximately 10 mm to approximately 14 mm, and the inner diameter, $d_2$, can range between approximately 9 mm to approximately 13 mm. While FIGS. 3A-3C illustrate the body 302 and the conduit 308 having a circular cross-section with a constant diameter over the length, $l_1$, of the body, one skilled in the art will realize that portions of the body 302 and the conduit 308 may be formed to different diameters as discussed below. Additionally, while FIGS. 3A-3C illustrate the body 302 and the conduit 308 as having a circular cross-section, one skilled in the art will realize that the body 302 and the conduit 308 may be formed having any cross-sectional shape.

Figure 3D:
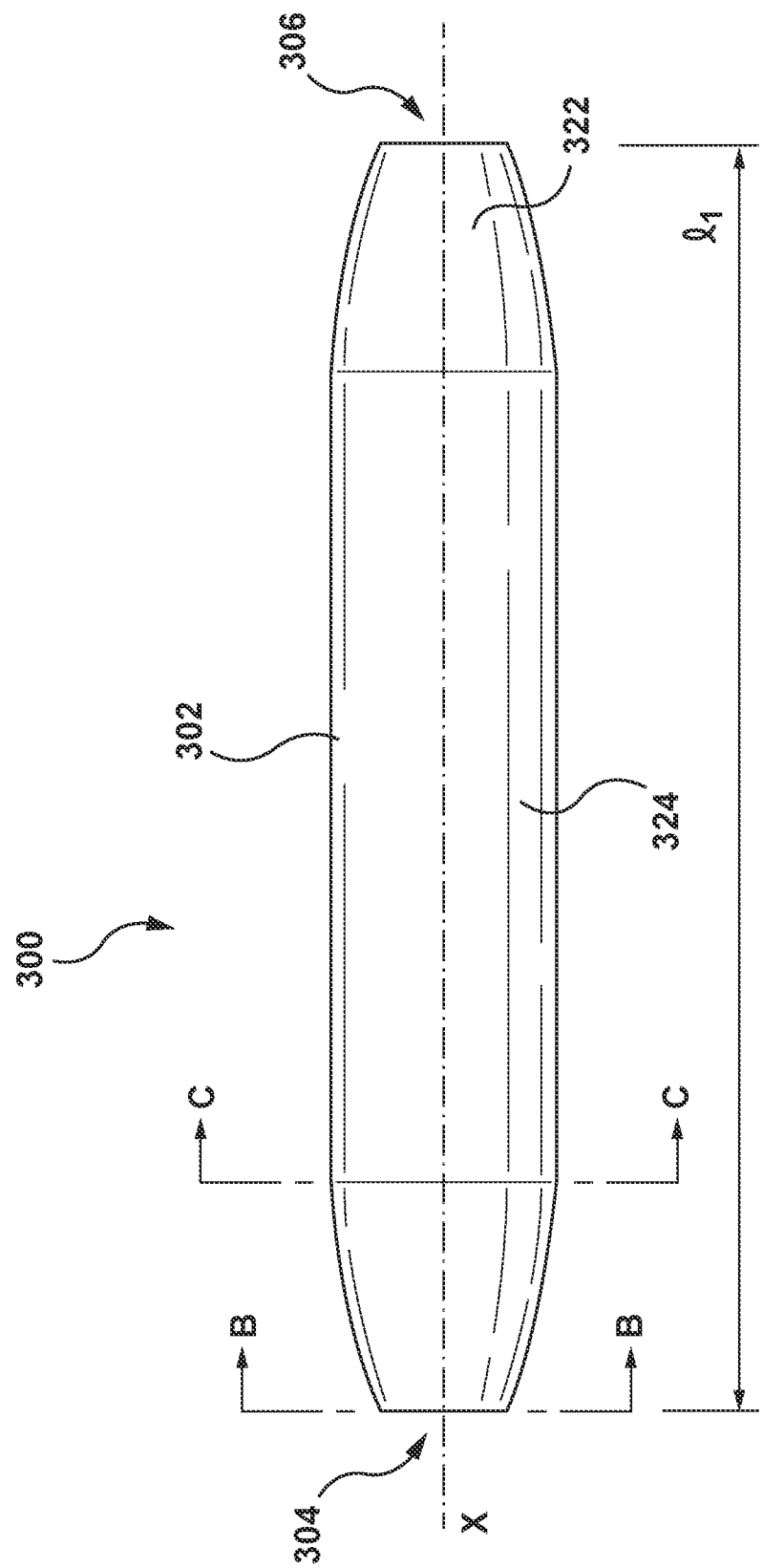

FIG. 3D is a side view that illustrates another example of the guide system 300. As illustrated, in this embodiment, the body 302 includes a central portion 324 with a first tapered portion 320 and a second tapered portion 322 located at opposing ends of the central portion 324. The first tapered portion 320 is located at the first end 304. The second tapered portion 322 is located at the second end 306. The first tapered portion 320 tapers, e.g., reduces in cross-sectional diameter, from a central portion 324 of the body 302 to the first end 304. The second tapered portion 322 tapers, e.g., reduces in cross-sectional diameter, from the central portion 324 of the body 302 to the second end 306. In this embodiment, the first tapered portion 320 and the second tapered portion 322 can minimize traumatic contact with the implantable medical device. That is, because the guide system 300 tapers from the central portion 324 of the body 302 to the first end 304 and the second end 306, the guide system 300 can be inserted into the central lumen of an implantable medical device and reduce force applied to the components of the implantable medical device. For example, when inserted into a prosthetic heart valve 200, the first tapered portion 320 and/or the second tapered portion 322 can reduce the force applied to the valve structure 204 including the leaflets 206.

In embodiments, the length, $l_1$, of the body 302 can be any length that allows the guide system 300 to fit within an implantable medical device and extend beyond the ends of the implantable medical device, as discussed above with reference to FIGS. 3A-3C. FIG. 3E illustrates a cross-sectional view of the guide system 300 taken along the line B at the first end 304. As illustrated, the first end 304 of the guide system 300 defines one opening of the conduit 308 having an approximate circular cross-section. The first tapered portion 320 can be formed having a frusto-conical shape. The first end 304 can be formed having an outer diameter, $d_3$, and an inner diameter, $d_3$. In embodiments, the outer diameter, $d_3$, of the first end 304 can be any diameter that allows the guide system 300 to fit within an implantable medical device, e.g., the first end 304 to fit within the central lumen of the prosthetic heart valve 200. Likewise, the inner diameter, $d_4$, can be any diameter that allows a distal portion of the delivery system to be inserted into the first end 304, e.g., allows the circumference of the distal portion 104 of the delivery system 100 including the retention members 122 to fit within the first end 304. For example, the outer diameter, $d_3$, can range between approximately 10 mm to approximately 14 mm, and the inner diameter, $d_4$, can range between approximately 9 mm to approximately 13 mm. While not illustrated, the second end 306 can be formed having an approximate circular cross-section with the second tapered portion 322 having a frusto-conical shape and can be formed having an outer diameter, $d_3$, and an inner diameter, $d_4$, similar to first end 304.

Figure 3F:
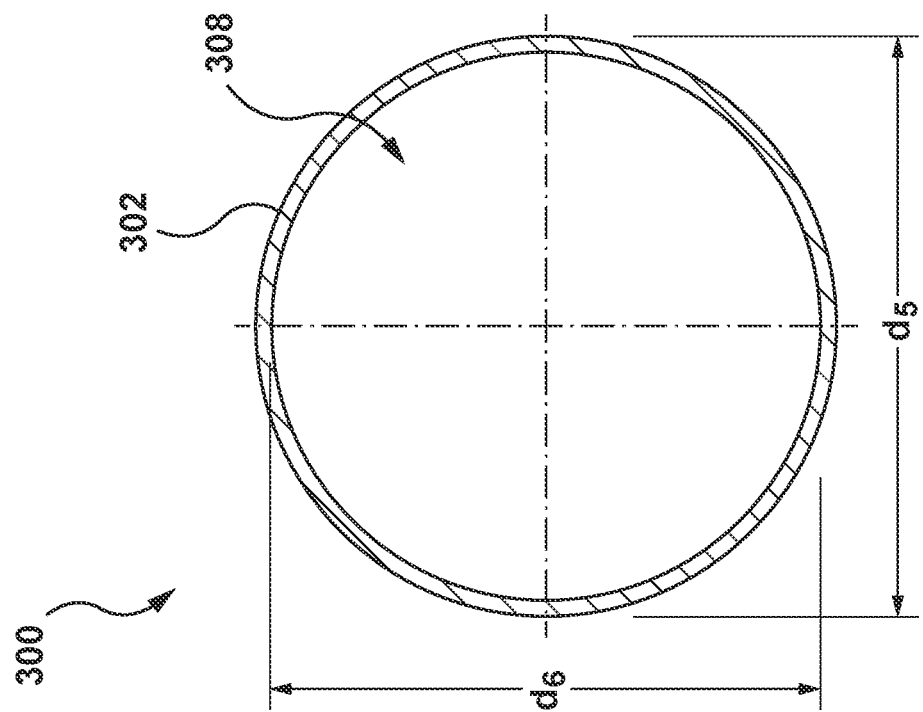
Figure 3E:
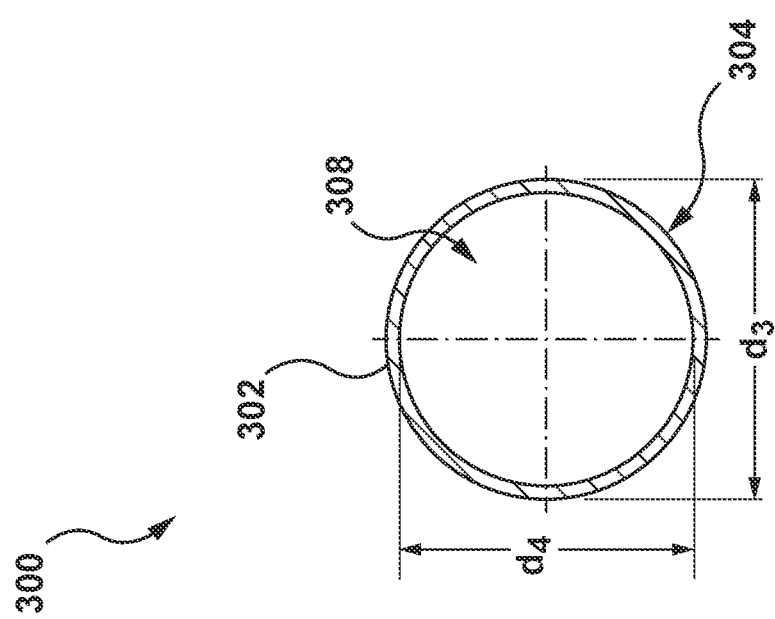

FIG. 3F illustrates a cross-sectional view of the guide system 300 taken along the line C at an intersection of the first tapered portion 320 and the central portion 324. As illustrated, the central portion 324 of the guide system 300 is formed in a cylindrical shape having an approximately circular cross-section. The central portion 324 defines the conduit 308 having an approximate circular cross-section. The central portion 324 can be formed having an outer diameter, $d_5$, and an inner diameter, $d_6$. As such, a maximum diameter of the conduit 308 can correspond to the inner diameter, $d_6$. In embodiments, the outer diameter, $d_5$, of the central portion 324 can be any diameter that allows the guide system 300 to fit within an implantable medical device, e.g., allows the central portion 324 to fit within the central lumen of the prosthetic heart valve 200. Likewise, the inner diameter, $d_6$, can be any length that allows a distal portion of the delivery system to be inserted into the conduit 308 e.g., allows the circumference of distal portion 104 of the delivery system 100 including the retention members 122 to fit within the central portion 324 of the body 302. For example, the outer diameter, $d_5$, can range between approximately 10 mm to approximately 21 mm, and the inner diameter, $d_6$, can range between approximately 9 mm to approximately 20 mm. While FIGS. 3D-3F illustrate the central portion 324 having a circular cross-section with a constant diameter over the length of the body, one skilled in the art will realize that portions of the central portion 324 may be formed to different diameters.

Figure 3G:
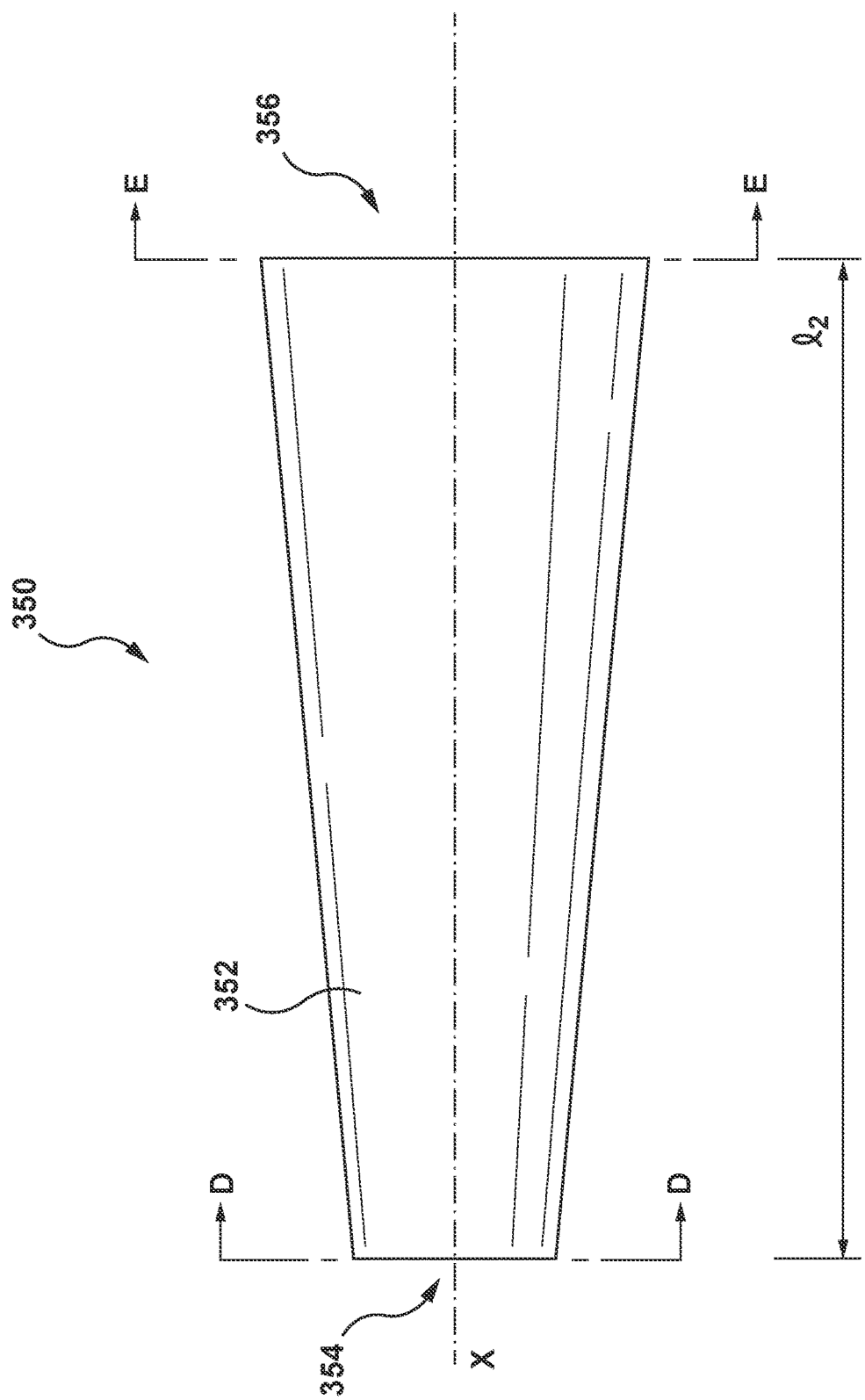
Figure 4:
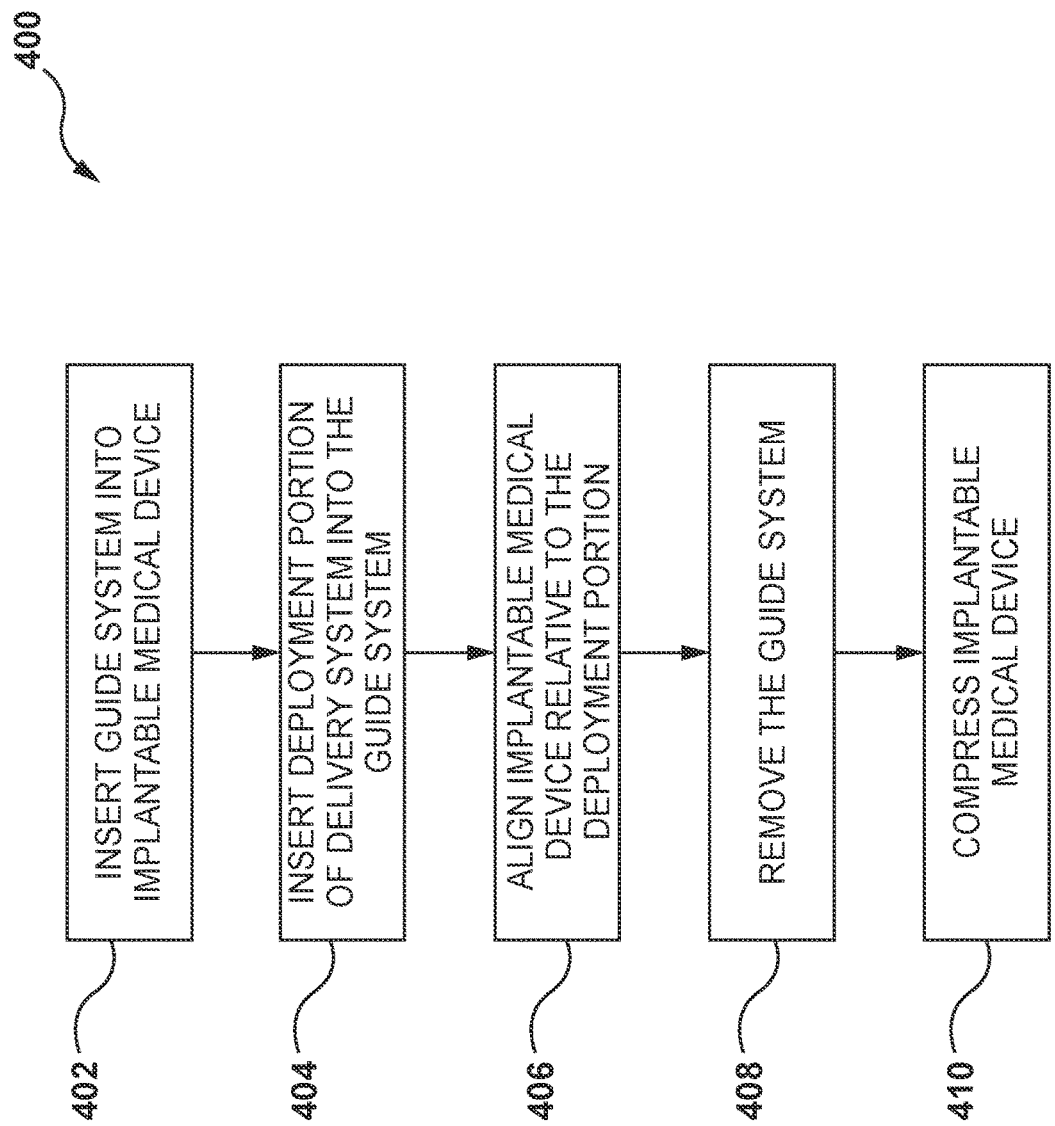
FIG. 4 and FIGS. 5A-5G depict an operation of the loading system of FIG. 3A-3I, according to an embodiment hereof.

FIG. 3G is a side view that illustrates another example of the guide system 350. The guide system 350 include a body 352 having a first end 354 and a second end 356. As illustrated, the guide system 350 can be formed in a frusto-conical shape in which the body 352 increases in diameter from the first end 354 to the second end 356. As such, the body 352 defines a conduit 358 having a funnel shape. In some embodiments, as illustrated, the body 352 can increase in diameter at a constant rate from the first end 354 to the second end 356 thereby having a linear slope from the first end 354 to the second end to the second end 356. In some embodiments, the body 352 can increase in diameter at various steps along the length of the body 352. In embodiments, the length, $l_2$, of the body 352 can be any length that allows the guide system 350 to fit within an implantable medical device and extend beyond the ends of the implantable medical device, as discussed above. For example, the length, $l_2$, can range between approximately 21 mm to approximately 34 mm.

In this embodiment, the frusto-conical shape of the body 352 can minimize traumatic contact with the implantable medical device. That is, because the body 352 tapers from the first end 354 to the second end 306, the first end 354 of guide system 350 can be inserted into the central lumen of an implantable medical device and minimize the force applied to the components of the implantable medical device. For example, when inserted into the prosthetic heart valve 200, the reduced diameter of the first end 354 can minimize the force applied to the valve structure 204 including the leaflets 206. Additionally, as the guide system 350 is inserted into the prosthetic heart valve 200, the increasing diameter of the body 302 can apply additional force on the leaflets 206, thereby orienting the leaflets 206, e.g., positioning the leaflets towards the outflow end 214 in an open state. Additionally, the frusto-conical shape can provide an operational advantage by indicating to a user which side of the body 352 is to be inserted into the implantable medical device, e.g., the first end 354.

FIG. 3H illustrates a cross-sectional view of the guide system 350 taken along the line D at the first end 354. As illustrated, the first end 354 of the guide system 350 is formed having an approximately circular cross-section. The first end 354 defines one opening of the conduit 358 having an approximate circular cross-section. The first end 354 can be formed having an outer diameter, $d_7$, and an inner diameter, $d_5$. In embodiments, the outer diameter, $d_7$, of the first end 354 can be any diameter that allows the guide system 350 to fit within an implantable medical device, e.g., allows the first end 354 to fit within the central lumen of the prosthetic heart valve 200. Likewise, the inner diameter, $d_8$, can be any diameter that allows a distal portion of the delivery system to pass through the first end 354, e.g., allows the circumference of distal portion 104 of the delivery system including the retention members 122 to fit within the first end 354. For example, the outer diameter, $d_7$, can range between approximately 10 mm to approximately 14 mm, and inner diameter, $d_8$, can range between approximately 9 mm to approximately 13 mm.

FIG. 3I illustrates a cross-sectional view of the guide system 350 taken along the line E at the second end 356. As illustrated, the second end 356 of the guide system 350 is formed having an approximately circular cross-section. The second end 356 defines a second opening of the conduit 358 having an approximate circular cross-section. The second end 356 can be formed having an outer diameter, $d_9$, and an inner diameter, $d_{10}$. As such, a maximum diameter of the conduit 358 can correspond to the inner diameter, $d_{10}$. In embodiments, the outer diameter, $d_9$, of the second end 356 can be any diameter that allows the guide system 350 to fit within an implantable medical device, e.g., the second end 356 to fit within the central lumen of the prosthetic heart valve 200. Likewise, the inner diameter, $d_{10}$, can be any diameter that allows a distal portion of the delivery system to be inserted into the second end 356, e.g., allows the circumference of distal portion 104 of the delivery system 100 including the retention members 122 to fit within the second end 356. For example, the outer diameter, $d_9$, can range between approximately 10 mm to approximately 20 mm, and the inner diameter, $d_{10}$, can range between approximately 11 mm to approximately 21 mm.

In any of the embodiments described above, the guide system 300 can be formed from any material such as metals, metal allows, or synthetic materials, such as plastics. In some embodiments, when constructed of synthetic materials such as plastics, the body 104 of the guide system 300 can include perforations formed in one or more lines along the long axis, x, of the body 302 from the first end 304 to the second end 306. Likewise, the guide system 350 can include perforations formed in one or more lines along the long axis, x, of the body 352 from the first end 354 to the second end 356. The perforations can allow the body 350 or the body 352 to be separated into multiple pieces. This can allow the guide system 300 or the guide system 350 to be removed after usage as described below in further detail.

FIGS. 4 and 5A-5F illustrate an example of a method 400 for loading an implantable medical device onto a delivery system using the guide system 300, in accordance with an embodiment hereof. One skilled in the art will realize that FIGS. 4 and 5A-5F illustrate one example of a method using the guide system 300 and that operations illustrated in FIG. 4 may be removed and/or additional operations may be added to the method 400. Moreover, while the method 400 is described with reference to the guide system 300, the method 400 can be performed using the guide system 350.

Figure 5A:
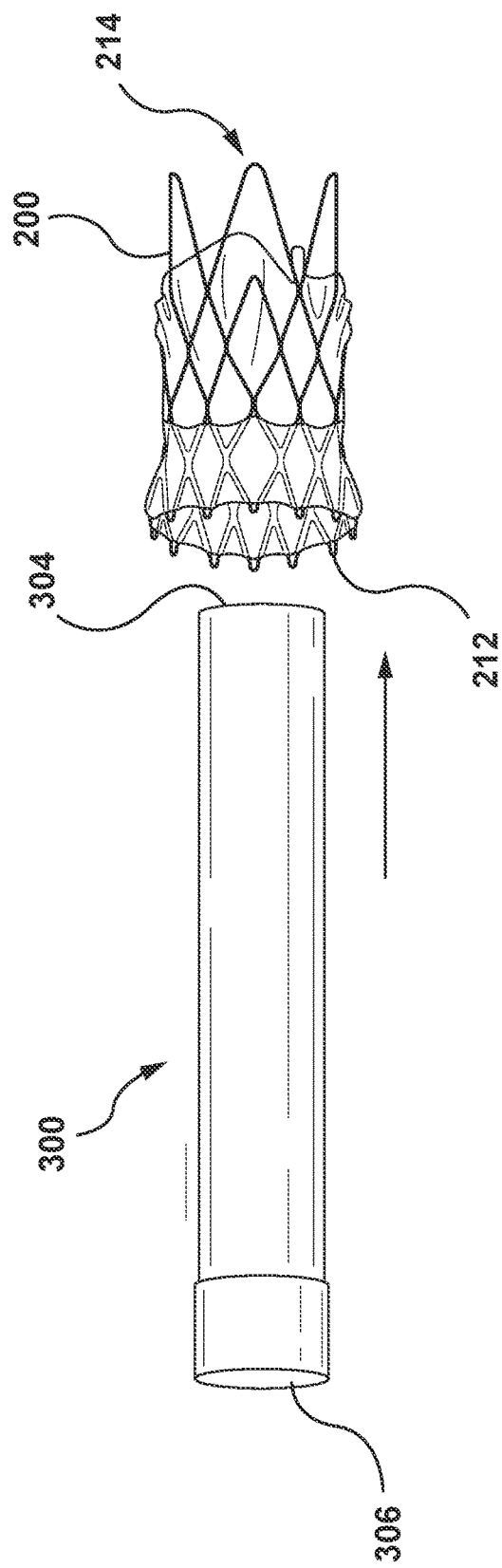
Figure 5B:
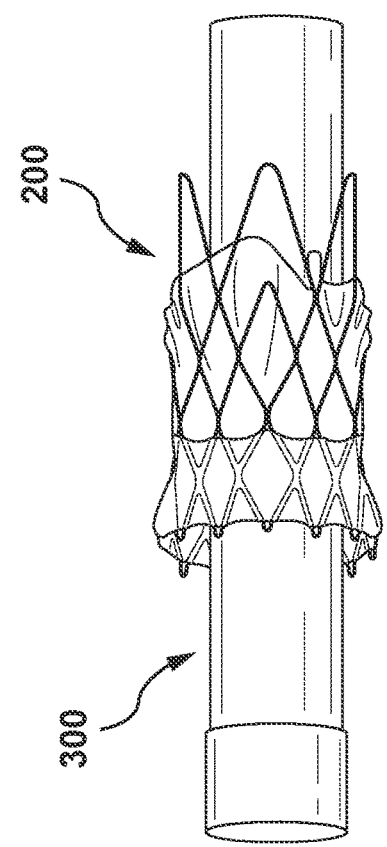
Figure 5C:
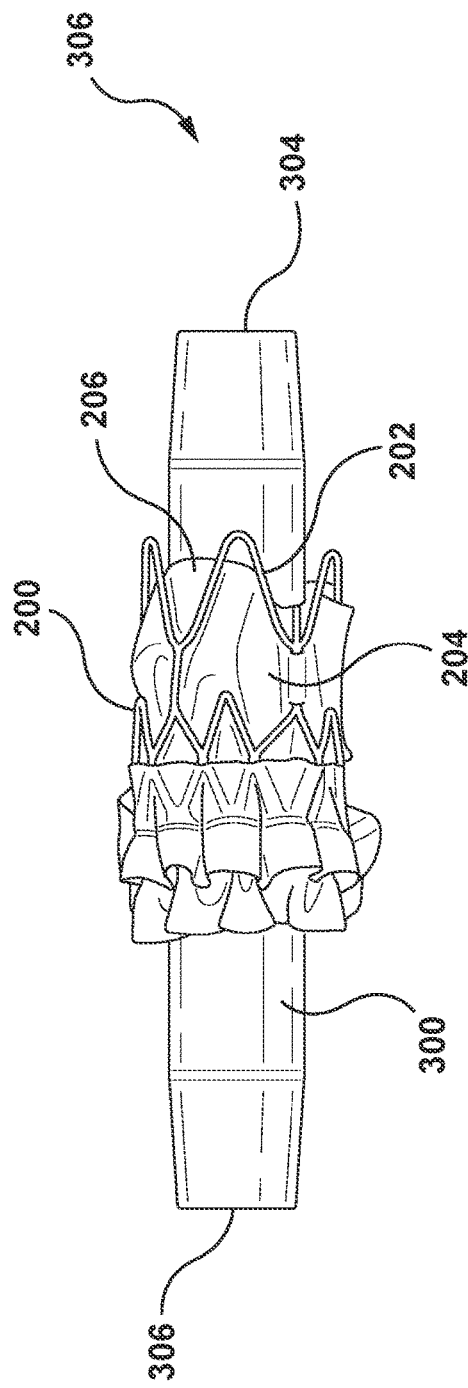

In step 402, a guide system can be inserted into an implantable medical device. For example, as illustrated in FIG. 5A, the guide system 300 can be inserted into the prosthetic heart valve 200. In this example, the first end 304 of the guide system 300 can be inserted into the inflow end 212 of the prosthetic heart valve 200. The guide system 300 can be passed through the central lumen of the prosthetic heart valve 200 until the first end 304 of the guide system passes out of the outflow end 214 of the prosthetic heart valve 200, as illustrated in FIG. 5B. As discussed above, the guide system 300 fits inside the central lumen of the prosthetic heart valve 200 to provide a conduit for inserting the delivery system 100 such that the guide system 300 protects the valve structure 204 and sent 302 from damage by the delivery system 100. That is, the guide system 300 can be advanced through the prosthetic heart valve 200 until the first end 304 and the second end 306 are positioned outside the prosthetic heart valve 200, as illustrated in FIG. 5C.

Additionally, as the guide system 300 is inserted through the prosthetic heart valve 200, the first end 304 of the guide system 300 applies a force on the leaflets 310 of the prosthetic heart valve 200. The force moves and directs the leaflets radially outwards and towards the outflow end 214 of the prosthetic heart valve 200, thereby into an open state.

Figure 5D:
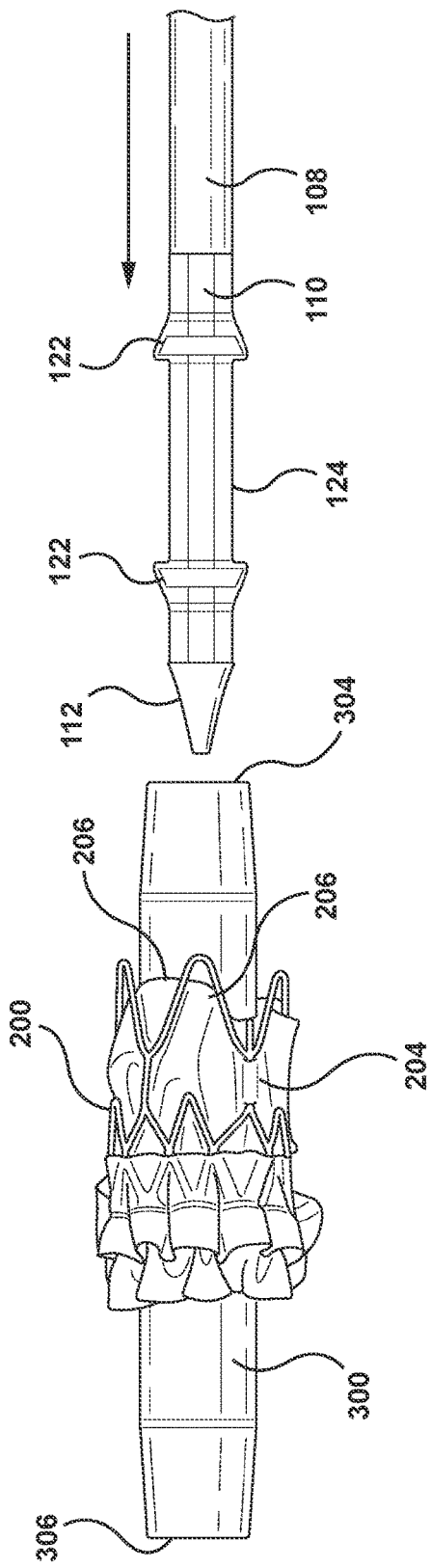

In step 404, a distal portion of the delivery system is inserted into the guide system. For example, as illustrated in FIG. 5D, the prosthetic heart valve 200 may be intended to be loaded onto the distal portion of the delivery system 100 with the outflow end 214 of the prosthetic heart valve 200 oriented towards the handle portion 206 and the inflow end 212 oriented towards the distal end of the catheter portion 102. As such, the distal portion 104 of the delivery system 100 can be inserted into the first end 304 of the guide system 300, which corresponds to the outflow end 214 of the prosthetic heart valve 200. The distal portion 104 can be advanced through the conduit 308 until the prosthetic heart valve 200 is positioned between the retention members 122 of the delivery system 100.

As the distal portion 104 of the delivery system 100 is inserted, the guide system 300 operates as a buffer between the distal portion 104 of the delivery system 100 and the prosthetic heart valve 200. That is, because the guide system 300 fills the central lumen of the prosthetic heart valve 200 as the distal portion 104 is inserted, the distal portion 104 and other portions of the delivery system 100 only contact the inner surfaces of the guide system 300 and do not contact the prosthetic heart valve 200.

In step 406, the implantable medical device is aligned relative to the distal portion of the delivery system. For example, the distal portion 104 can be advanced or retracted within the conduit 308 until the prosthetic heart valve 200 is aligned so that it is between the retention members 122.

Figure 5E:
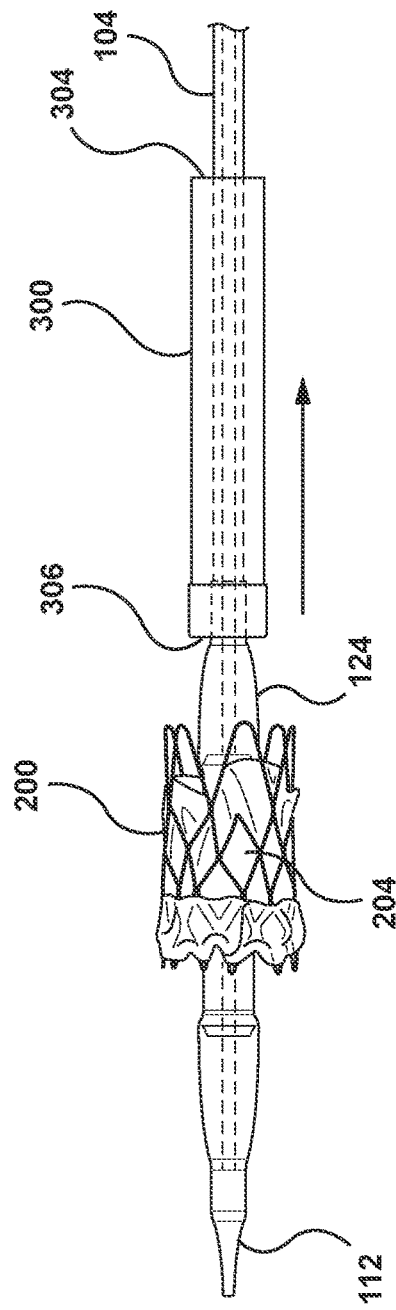
Figure 5F:
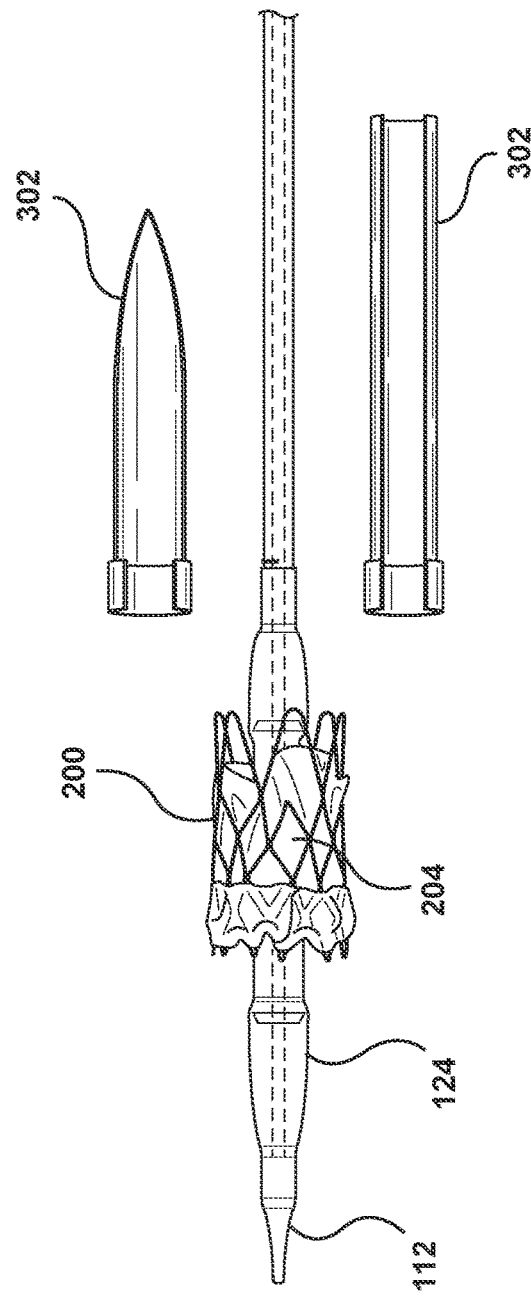

In step 408, the guide system is removed. For example, as illustrated in FIG. 5E, the guide system 300 can be advanced in the direction of the first end 304 towards the proximal end of the catheter portion 102 to remove the guide system 300 from the central lumen of the prosthetic heart valve 200. The guide system 300 can continue to be advanced in the proximal direction of the delivery system 100 along the catheter portion 202 of the delivery system 100. In some embodiments, the guide system 300 can be removed once the prosthetic heart valve 200 is compressed onto the distal portion 104 of the delivery system 100. That is, once the prosthetic heart valve 200 is radially compressed onto the distal portion of the delivery system, the guide system 300 can be retracted towards the distal end of the catheter portion 102 thereby passing the prosthetic heart valve 200 in the compressed state through the conduit 308. In some embodiments, if the guide system 300 includes perforations, the body 302 of the guide system 300 can be separated into multiple pieces to remove the guide system 300, as illustrated in FIG. 5F.

Figure 5G:
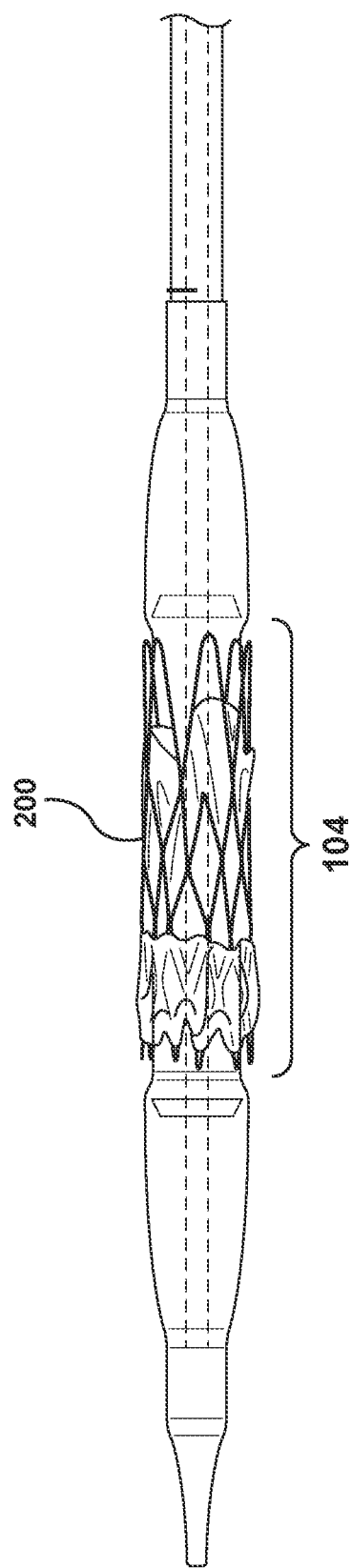

In step 410, the implantable medical device can be radially compressed onto the delivery system. For example, the prosthetic heart valve 200 aligned with the distal portion 104 can be inserted into a crimper chamber of a crimper. The crimper can be operated to radially compress the prosthetic heart valve 200 onto the distal portion 104, for example, as illustrated in FIG. 5G, which shows the distal portion 104 of the delivery system 100 with the prosthetic heart valve 200 crimped thereon.

FIGS. 6A-6F illustrate examples of a guide system 600 in accordance with an embodiment hereof. One skilled in the art will realize that FIGS. 6A-6F illustrate one example of a guide system and that existing components illustrated in FIGS. 6A-6F may be removed and/or additional components may be added to the guide system 600.

Figure 6A:
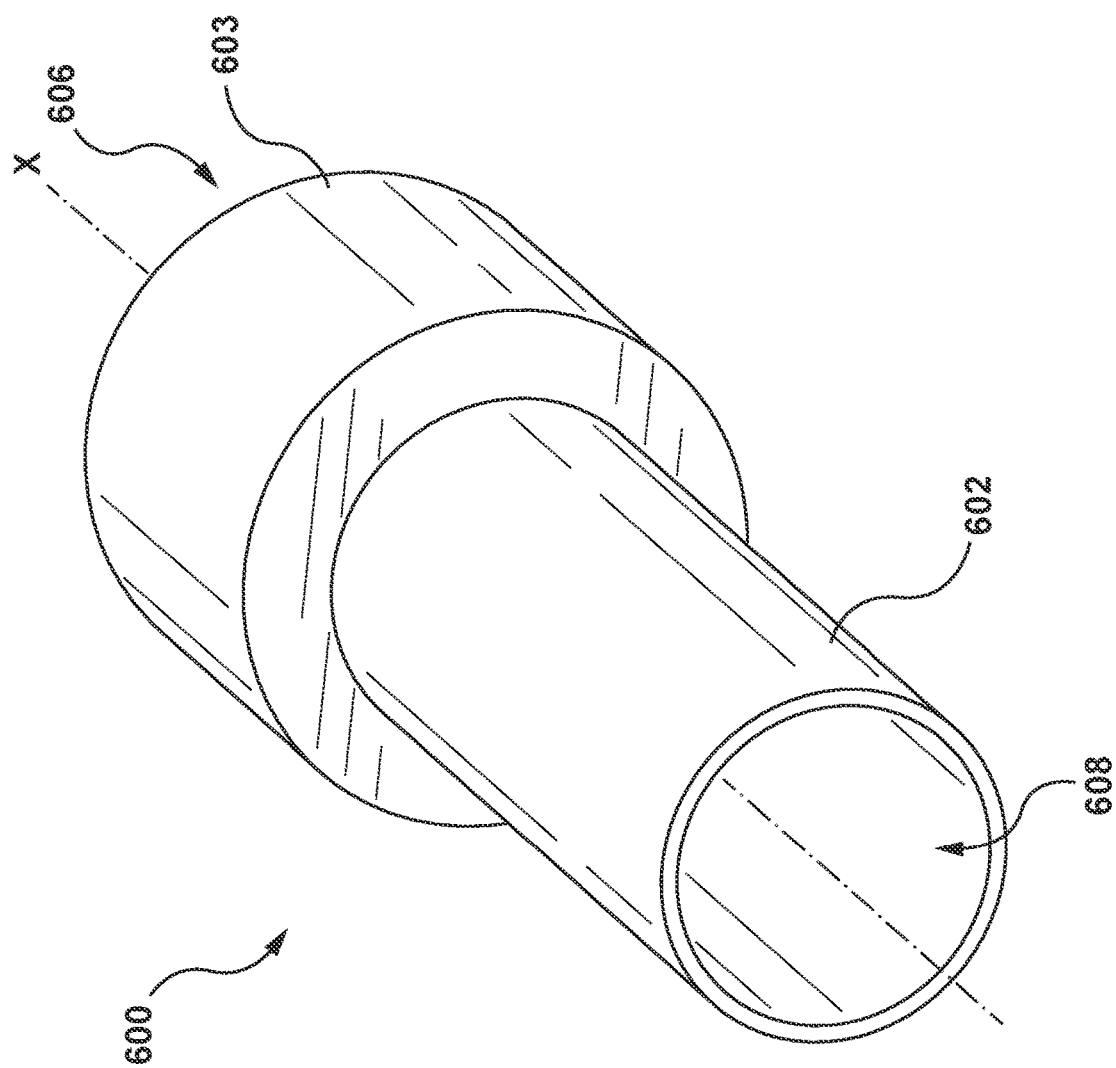
FIGS. 6A-6H depict several illustrations of another guide system for use with an implantable medical device, according to an embodiment hereof.
Figure 6B:
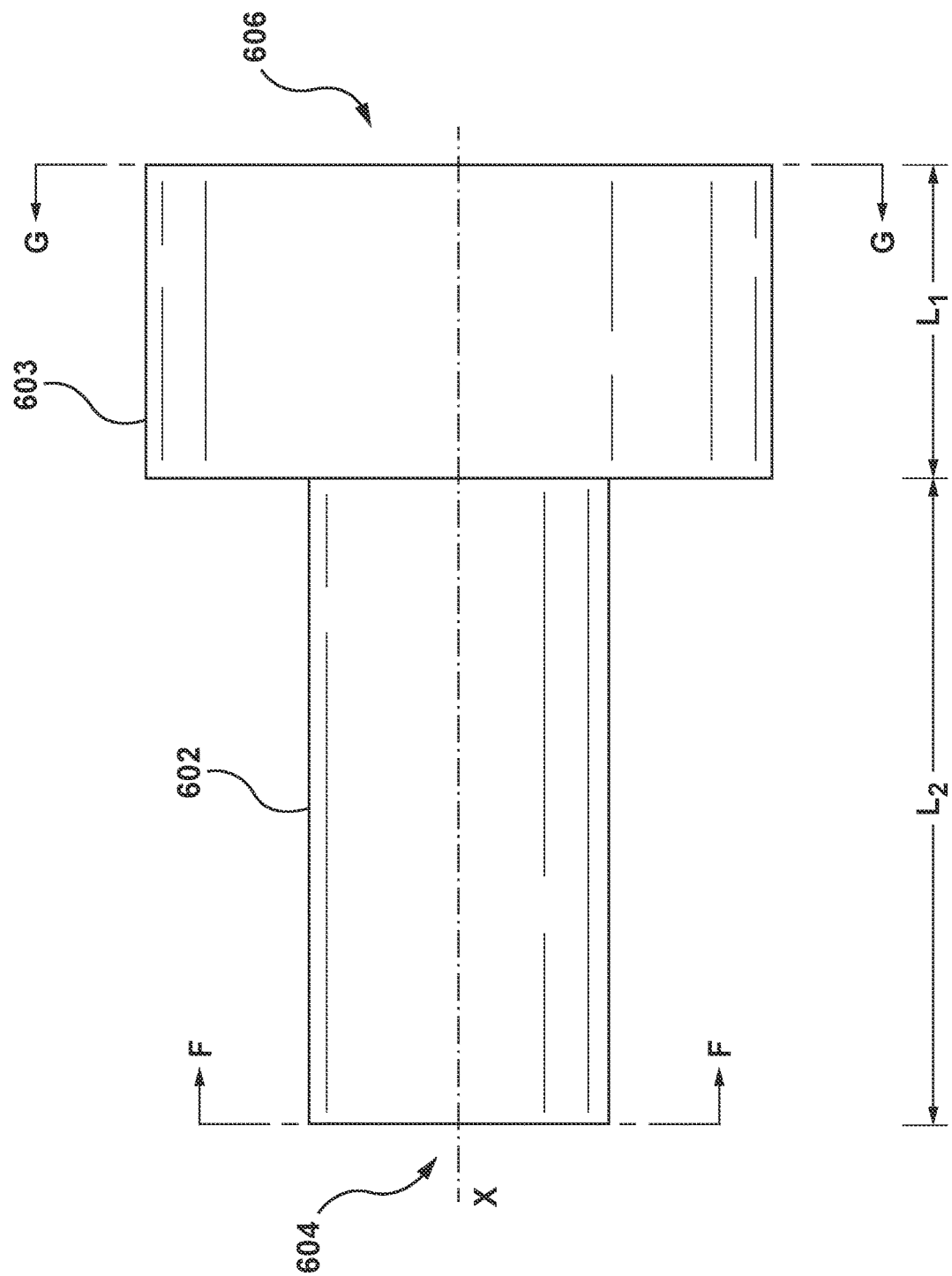

As disclosed herein, the guide system 600 can be utilized on implantable medical devices (e.g., a prosthetic heart valve 200 as described above with reference to FIGS. 2A-2D) that are to be loaded and delivered translumimally via portions of a delivery system (e.g., via a delivery system 100 as described above with reference to FIGS. 1A and 1B). As illustrated in FIG. 6A, which is a perspective view, the guide system 600 includes a body 602 with a first end 604, and a base 603 with a second end 606. The body 602 and the base 603 can be formed having a hollow cylindrical shape thereby defining a conduit 608. As illustrated in FIG. 6B, which is a side view of the guide system 600, the base 603 can be formed having a length, $L_1$, that is measured along a long axis, x, of the guide system 600. The body 602 can be formed having a length, $L_2$, that is measured along a long axis, x, of the guide system 600.

Figure 6D:
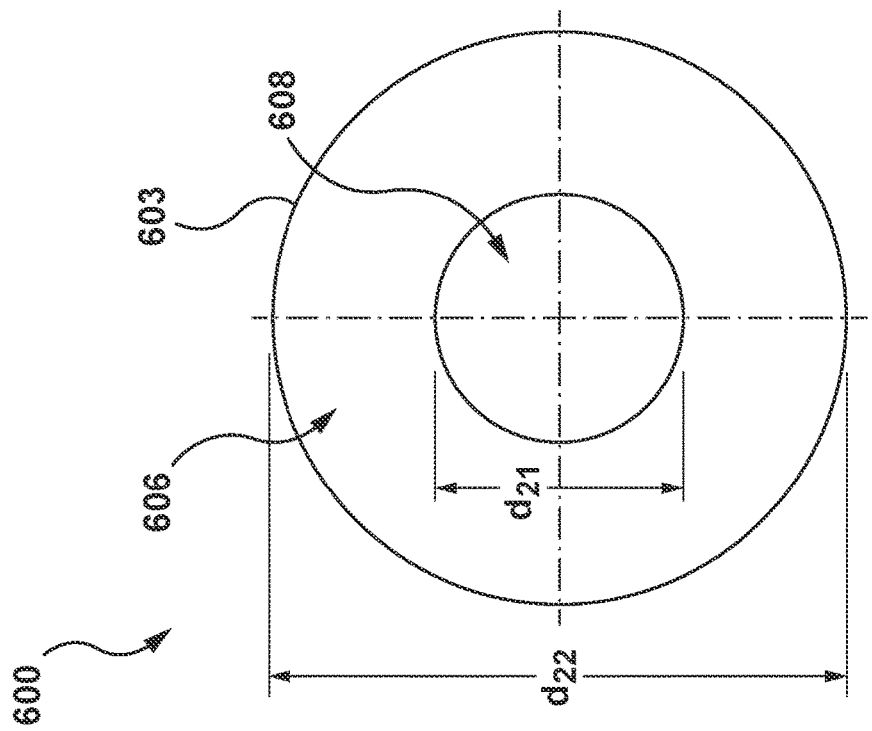

In embodiments, the length, $L_2$, of the body 602 can be any length that allows the guide system 600 to fit within an implantable medical device and extend to engage components of the implantable medical device. The body 602 operates as a buffer to allow a delivery system to be inserted into the implantable medical device while reducing contact with the components of the implantable medical device. For example, as illustrated in FIGS. 6E and 6F, the first end 604 of the guide system 600 can be inserted into the inflow end 212 of a prosthetic heart valve 200. The body 602 operates to enter the central lumen of the prosthetic heart valve 200 and provide a conduit for inserting the delivery device. The base 603 operates as a stop to abut the inflow end 212 of the prosthetic heart valve 200 and prevent further insertion of the body 602. In embodiments, the body 602 can extend into the central lumen of the prosthetic heart valve 200 to engage with the leaflets 206 sufficiently to open up a pathway for insertion of the delivery system, e.g., the distal portion 104, but not extend beyond ends of the leaflets 206. Because the body 602 does not extend beyond the ends of the leaflets 206, the guide system 300 can be inserted into the inflow end 212 of the prosthetic heart valve 200 to orient the leaflets 206 in an open state and then retracted from the inflow 312 without inverting the leaflets 206.

The length, $L_2$, of the body 602 can be a length that allows the body to extend into the central lumen of the prosthetic heart valve 200 without extending beyond the outflow end 214, when the base 603 abuts the inflow end 212 of the stent 202. For example, as illustrated in FIG. 6F, the length, $L_2$, of the body 602 can be a length such that first end 604 falls between axial positions 690 and 692 on the stent 202 of the prosthetic heart valve 200, when the base 603 abuts the stent 202. In some embodiments, the axial positions 690 and 692 can correspond to the commissure posts of the stent 202.

Figure 6C:
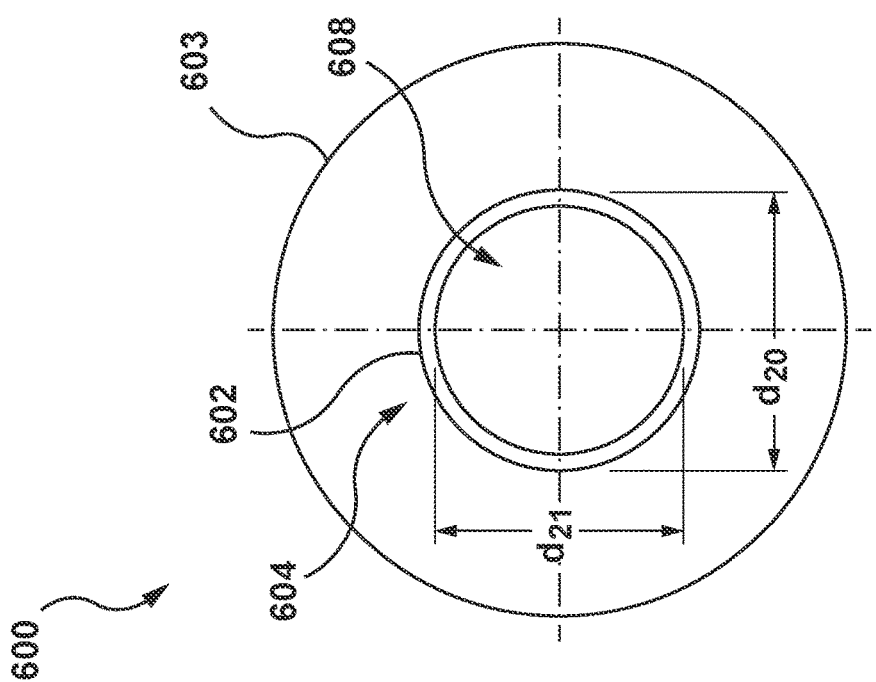
Figure 6E:
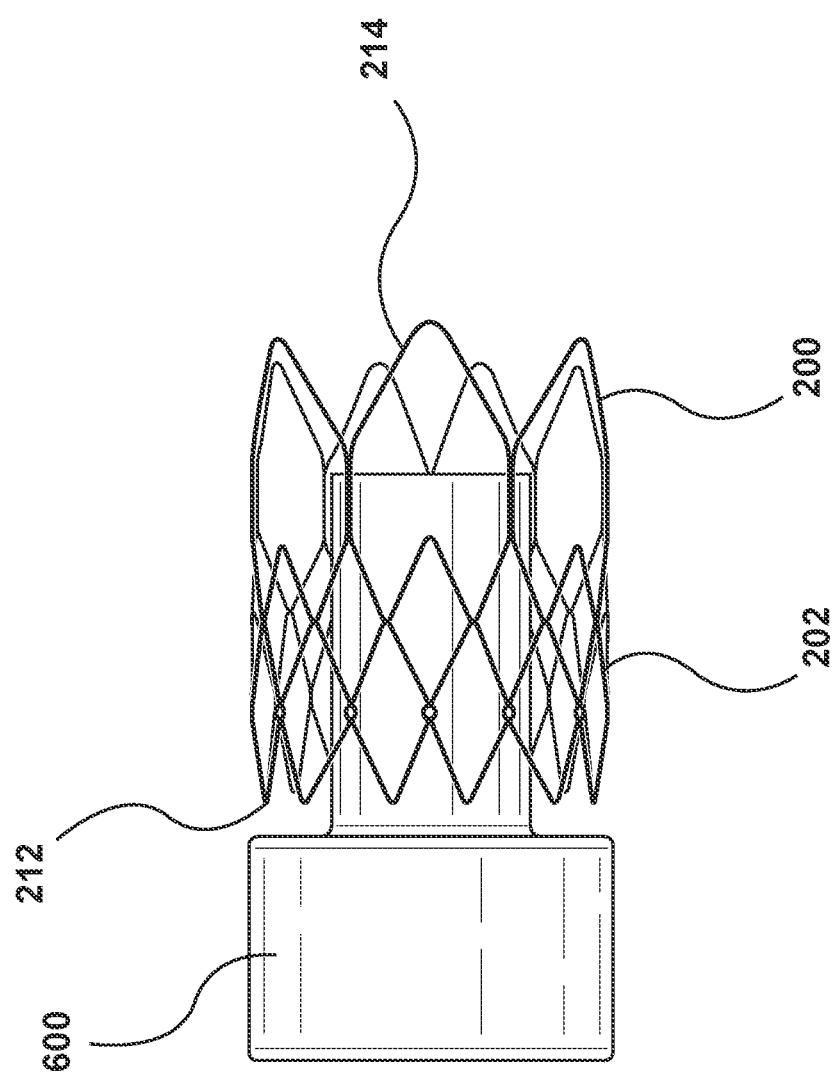
Figure 6F:
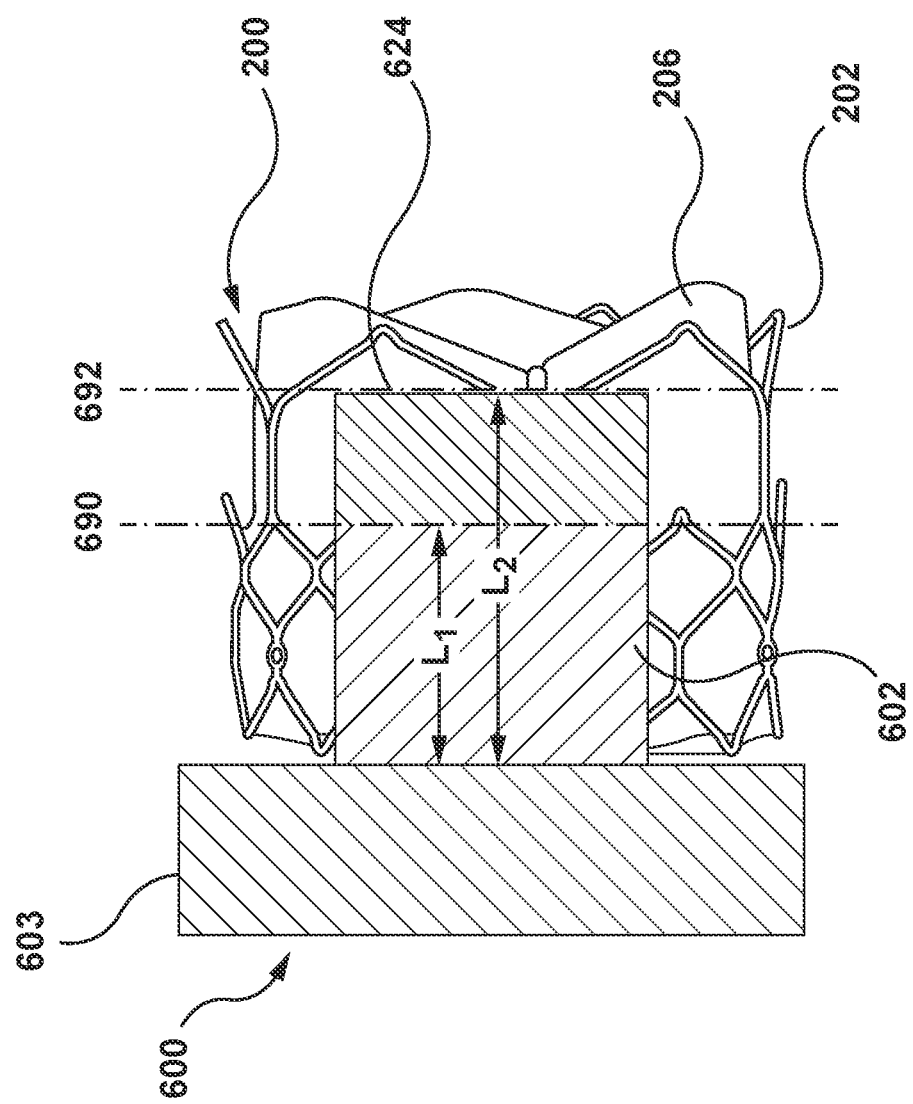

FIG. 6C illustrates a cross-sectional view of the guide system 600 taken along the line F at the first end 604. As illustrated, the first end 604 of the guide system 600 is formed having an approximately circular cross-section. The first end 604 defines one opening of the conduit 608 having an approximate circular cross-section. The first end 604 can be formed having an outer diameter, $d_{20}$, and an inner diameter, $d_{21}$. In embodiments, the outer diameter, $d_{20}$, of the first end 604 can be any diameter that allows the guide system 600 to fit within an implantable medical device, e.g., allows the first end 604 to fit within the central lumen of the prosthetic heart valve 200. Likewise, the inner diameter, $d_{21}$, can be any diameter that allows a distal portion of the delivery system to be inserted into the first end 604, e.g., allows the circumference of distal portion 104 of the delivery system 100 including the retention members 122 to fit within the first end 604. For example, the outer diameter, $d_{20}$, can range between approximately 10 mm to approximately 14 mm, and the inner diameter, $d_{21}$, can range between approximately 9 mm to approximately 13 mm.

FIG. 6D illustrates a cross-sectional view of the guide system 600 taken along the line F at the second end 606. As illustrated, the second end 606 of the guide system 600 is formed having an approximately circular cross-section. The second end 606 defines a second end of the conduit 608 having an approximate circular cross-section. The second end 606 can be formed having an outer diameter, $d_{22}$, (outer diameter of the base 603) and an inner diameter, $d_{21}$. As such, a diameter of the conduit 608 can correspond to the inner diameter, $d_{21}$. In embodiments, the outer diameter, $d_{22}$, of the second end 606 can be any diameter that allows the guide system 600 to abut the implantable medical device, e.g., to abut the stent 202 of the prosthetic heart valve 200 without entering the central lumen. In embodiments, the outer diameter, $d_{22}$, can be set in order to provide a gripping area for a user. For example, the outer diameter, $d_{22}$, can range between approximately 10 mm to approximately 22 mm. While FIGS. 6A-6D illustrate the conduit 608 having a circular cross-section with a constant diameter over the length of the body 602 and base 603, one skilled in the art will realize that portions of the body 602, the base 603, and the conduit 608 may be formed to different diameters.

As discussed above, the guide system 600 can operate to be inserted into the inflow end 212 of the prosthetic heart valve 200. In this embodiment, the guide system 600 can be utilized when loading the prosthetic heart valve 200 onto the delivery system 100 such that the inflow end 212 is positioned proximal to the distal end of the catheter portion 102. In this embodiment, the guide system 600 can be inserted into the prosthetic heart valve 200 and then removed from the distal end of the catheter portion 102 once the distal portion 206 of the delivery system 100 is inserted into the conduit 608.

Figure 6H:
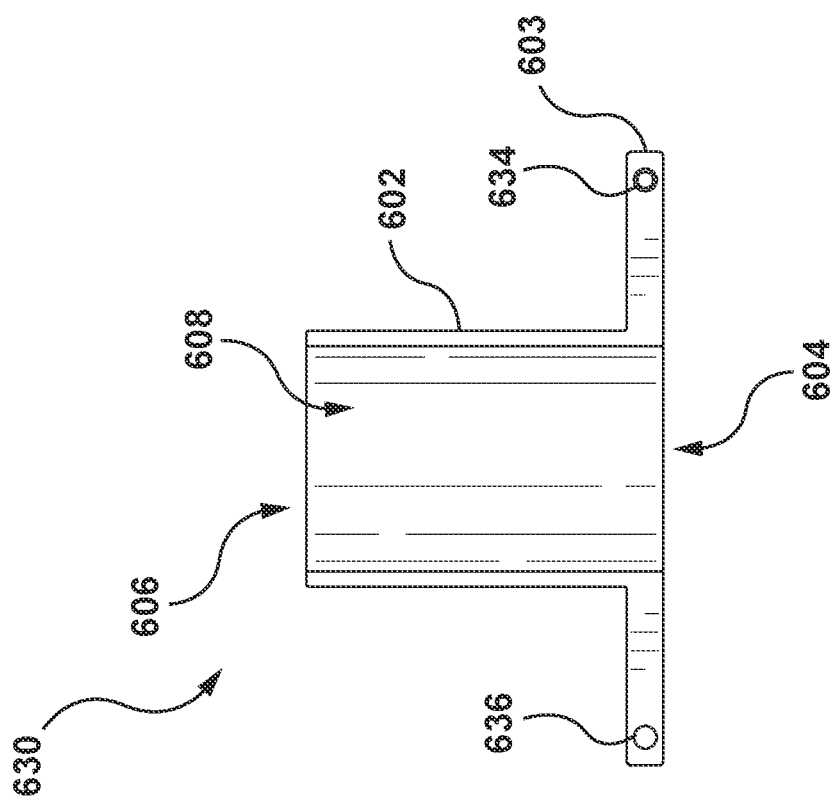
Figure 6G:
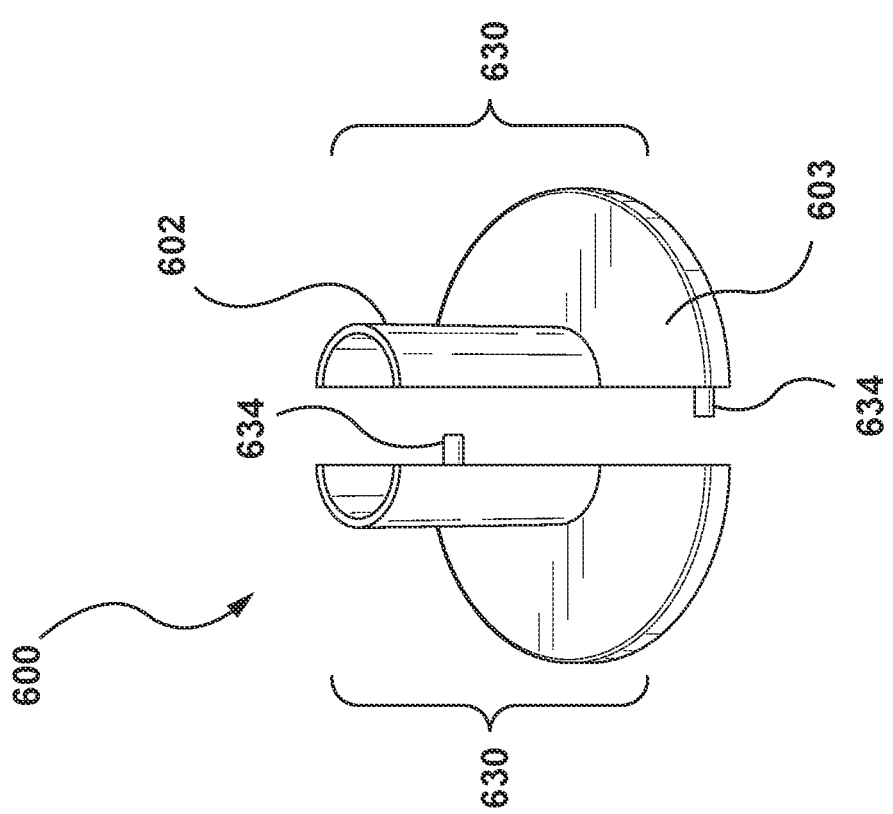

FIGS. 6G and 6H illustrate another example of the guide system 600. FIG. 6H is a side view that illustrates another example of the guide system 600. As illustrated in FIG. 6G, which is a perspective view, the guide system 600 can be split longitudinally into a first side 630 and a second side 632, each side comprising half of the body 602 and half of the base 603. As such, the guide system 600, which split, can assist with removal of the guide system 600 during the loading process. The guide system 600 is configured such that the first side 630 and the second side 632 can be joined and separated. For example, for insertion into the implantable medical device, the first side 630 and the second side 632 can be joined forming the guide system 600 and the conduit 608. Once the delivery system is inserted into the implantable medical device, the first side 630 and the second side 632 can be separated from removal from the delivery system.

As illustrated in FIG. 6G, each of the first side 630 and the second side 632 can include corresponding pins 634 and holes 636. For example, as illustrated in FIG. 6G, which is a side view of the first side 630, the base 603 can include a pin 634 positioned on one side of the conduit 608, and a hole positioned on the opposing side of the conduit 608. The pin 634 of the first side 630 engages with a hole 636 of the second side 632 when the first side 630 and second side 632 are joined. Likewise, the hole 636 of the first side 630 engage with a pin of the second side 632 when the first side 630 and the second side 632 are joined.

FIGS. 7A-7G illustrate examples of a guide system 700 in accordance with an embodiment hereof. One skilled in the art will realize that FIGS. 7A-7G illustrate one example of a guide system and that existing components illustrated in FIGS. 7A-7G may be removed and/or additional components may be added to the guide system 700.

Figure 7A:
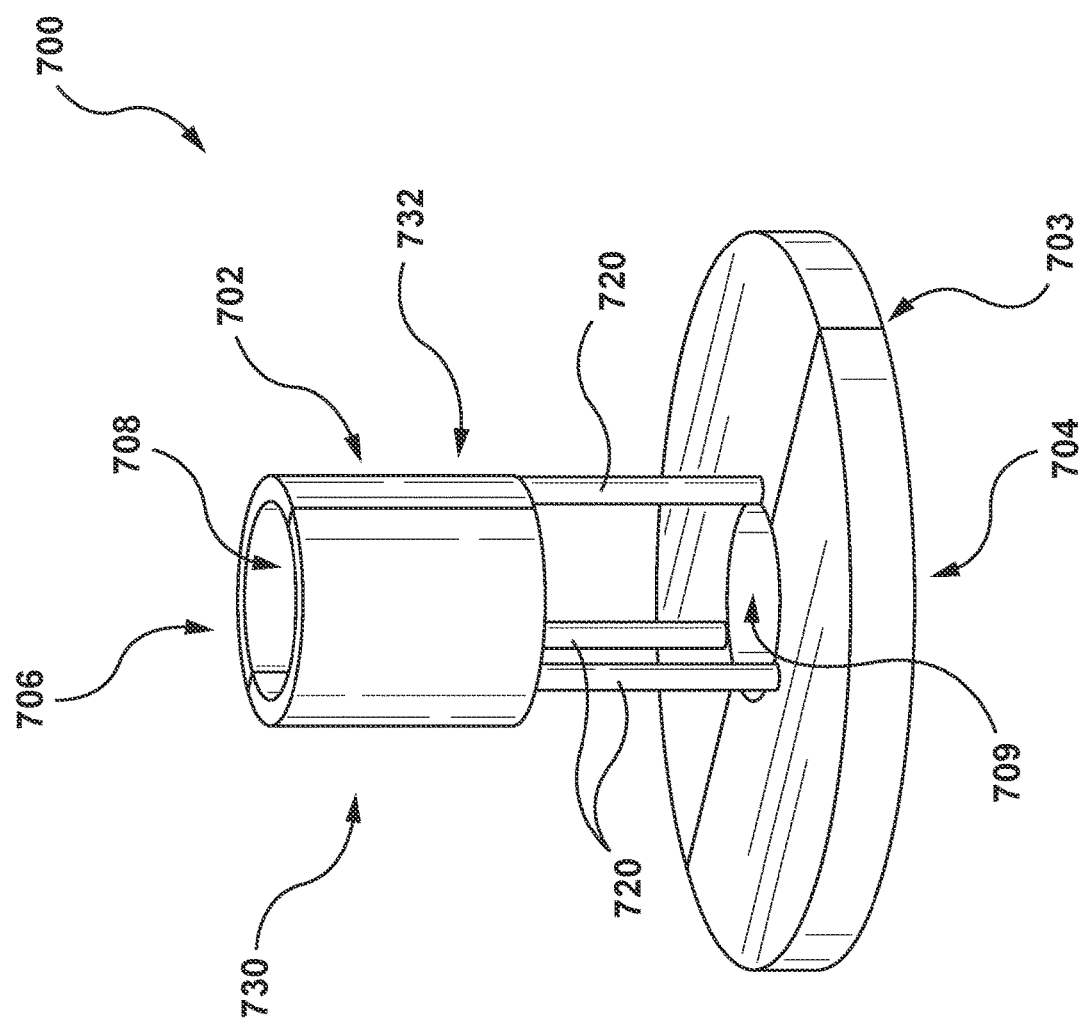
FIGS. 7A-7G depict several illustrations of another guide system for use with an implantable medical device, according to an embodiment hereof.

As disclosed herein, the guide system 700 can be utilized on implantable medical devices (e.g., prosthetic heart valves as described above with reference to FIGS. 2A-2D) that are to be loaded and delivered transluminally via portions of a delivery system (e.g., via a catheter as described above with reference to FIGS. 1A and 1B). As illustrated in FIG. 7A, which is a perspective view, the guide system 700 includes a body 702 with a first end 704, and a base 703 with a second end 706. The body 702 is connected to the base 703 by legs 720. For example, as illustrated, the body 702 can be connected to the base 703 by three (3) legs 720. The legs 720 define spaces 712 between the body 702 and the base 703.

Figure 7B:
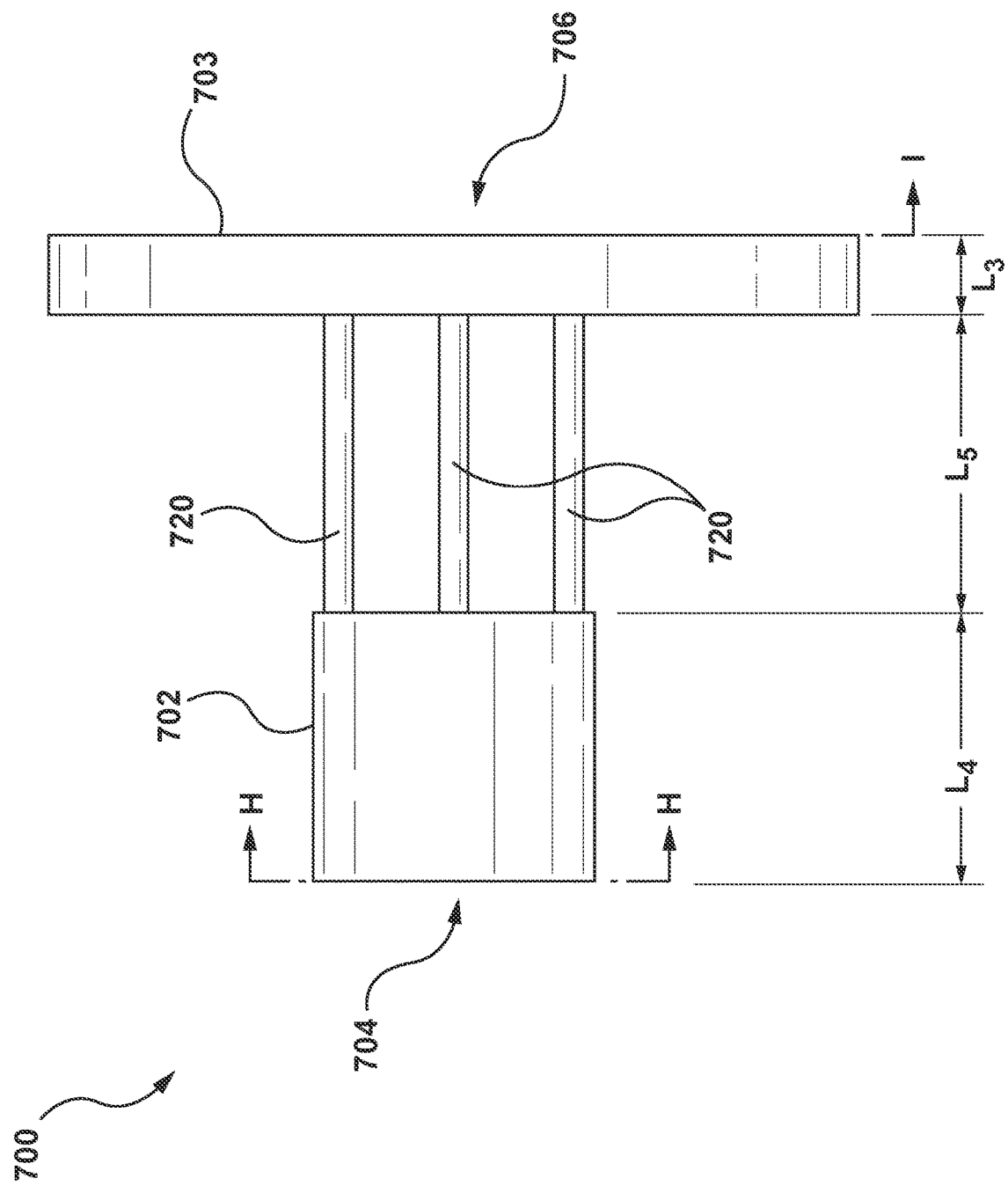

The body 702 and the base 703 can be formed having a hollow cylindrical shape thereby defining a conduit 708. As illustrated in FIG. 7B, which is a side view of the guide system 700, the base 703 can be formed having a length, $L_3$, that is measured along a long axis, x, of the guide system 700. The body 702 can be formed having a length, $L_4$, that is measured along a long axis, x, of the guide system 700. Each of the legs 720 can be formed having a length, $L_5$, that is measured along a long axis, x, of the guide system 700.

Figure 7D:
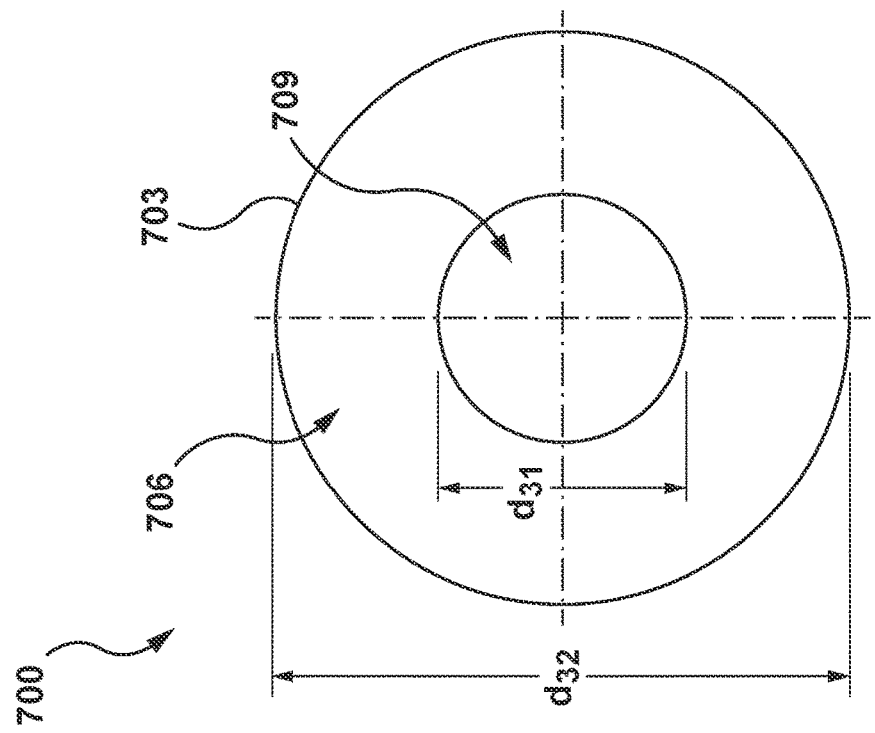

In embodiments, a combination of the length, $L_4$, of the body 702 and the length, $L_5$, of the legs 720 can be any length that allows the guide system 700 to fit within an implantable medical device, to extend to engage components of the implantable medical device, and to operate to allow a delivery system to be inserted into the implantable medical device without contacting the components of the implantable medical device. For example, as illustrated in FIGS. 7F, the first end 704 of the guide system 700 can be inserted into the outflow end 214 of a prosthetic heart valve 200. The body 702 operates to enter the central lumen of the prosthetic heart valve 200 and provide conduit for inserting delivery device. The base 703 operates as a stop to abut the outflow end 214 of the prosthetic heart valve 200 and prevent further insertion of the body 702. In embodiments, a combination of the length, $L_4$, of the body 702 and the length, $L_5$, of the legs 720 can be a length such that the body 702 extends into the central lumen of the prosthetic heart valve 200 and the first end 704 is positioned adjacent to the inflow end 212.

In this embodiment, once the body 702 is inserted into the central lumen of the prosthetic heart valve 200, the leaflets 206 of the prosthetic heart valve 200 can rest within the spaces 712 formed by the legs 720. As such, the leaflets 206 can rest in a closed state when the guide system 700 is inserted into the prosthetic heart valve 200. For example, once inserted into the prosthetic heart valve 200, the guide system 700 and the prosthetic heart valve 200 can be stored for later loading. For example, as illustrated in FIG. 7G, the guide system 700 and the prosthetic heart valve 200 can be stored in a jar 750. The jar 750 can include a body 752, a lid 754, and a sterile liquid filling the body 752.

In embodiments, the prosthetic heart valve 200 may be installed on the guide system 700 such that the prosthetic heart valve 200 is propped up on guide system 700 with the legs 720 being aligned within commissure connections on the prosthetic heart valve 200. The length of the body 702 can be long enough so that the body 702 extends along the length of an inflow portion of the prosthetic heart valve 200. The configuration of the guide system 700 allows the guide system 700 to be packaged with the prosthetic heart valve 200 already mounted thereon. Further, the legs 720 can keep contact off the surfaces of the leaflets 206 to minimize abrasion and rubbing. Additionally, the legs 720 may serve to connect the body 702 and the base 703 together, thereby creating a mount or stand for the prosthetic heart valve 200.

During loading onto a delivery system, the guide system 700 can operate to protect the prosthetic heart valve 200 from contact with the delivery system, for example, the distal portion 104 of the delivery system 100. Once the guide system 700 is retracted from the prosthetic heart valve 200, the guide system 700 can operate to move the leaflets 206 of the prosthetic heart valve 200 from a closed state to an open state. That is, as the guide system 700 is retracted from the outflow end 214 of the prosthetic heart valve 200, the body 704 can apply a force to the leaflets 206 to transition the leaflets 206 from the closed state to the open state.

For example, when a user aligns a delivery system for insertion into the guide system 700, the user may first pull the guide system 700 by the base 703 towards a proximal end of the prosthetic heart valve 200, thereby opening up the leaflets 206 on the prosthetic heart valve 200. As such, the delivery system then can be safely inserted through the opening at second end 706. Moreover, inserting the guide system 700 through an outflow portion of the prosthetic heart valve 200 may provide advantages. An amount of contact with the leaflets 206 contact is reduced, thereby reducing the friction due to contact. Additionally, this movement keeps the leaflets 206 in tension towards a proximal end and may not encourage inversion the leaflets 206.

Figure 7C:
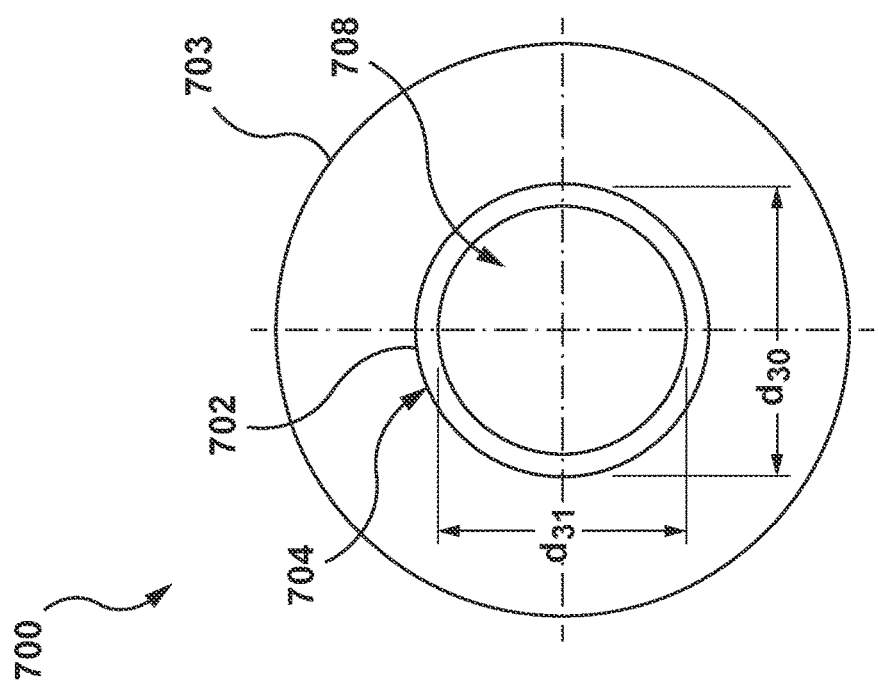

FIG. 7C illustrates a cross-sectional view of the guide system 700 taken along the line H at the first end 704. As illustrated, the first end 704 of the guide system 700 is formed having an approximately circular cross-section. The first end 704 defines one opening of the conduit 708 having an approximate circular cross-section. The first end 704 can be formed having an outer diameter, $d_{30}$, and an inner diameter, $d_{31}$. In embodiments, the outer diameter, $d_{30}$, of the first end 704 can be any diameter that allows the guide system 700 to fit within an implantable medical device, e.g., the first end 704 to fit within the central lumen of the prosthetic heart valve 200. Likewise, the inner diameter, $d_{31}$, can be any diameter that allows a distal portion of the delivery system to be inserted into the first end 704, e.g., the circumference of distal portion 104 including the retention members 122 fit within the first end 704. For example, the outer diameter, $d_{30}$, can range between approximately 10 mm to approximately 14 mm, and the inner diameter, $d_{31}$, can range between approximately 9 mm to approximately 13 mm.

FIG. 7D illustrates a cross-sectional view of the guide system 700 taken along the line I at the second end 706. As illustrated, the second end 706 of the guide system 700 is formed having an approximately circular cross-section. The second end 706 defines a second end 709 of the conduit 708 having an approximate circular cross-section. The second end 706 can be formed having an outer diameter, $d_{32}$, (outer diameter of the base 703) and an inner diameter, $d_{31}$. As such, a diameter of the second end 709 of the conduit 708 can correspond to the inner diameter, $d_{31}$. In embodiments, the outer diameter, $d_{32}$, of the second end 706 can be any diameter that allows the guide system 700 to abut the implantable medical device, e.g., abut the stent 702 of the prosthetic heart valve 200 without entering the central lumen. While FIGS. 7A-7D illustrate the conduit 708 having a circular cross-section with a constant diameter over the length of the body 702 and base 703, one skilled in the art will realize that portions of the body 702, the base 703, and the conduit 708 may be formed to different diameters.

Similar to guide system 600 discussed above, to assist with removal of the guide system 700 during the loading process, the guide system 700 can be split into a first side 730 and a second side 732, each side comprising half of the body 702 and the base 703. The guide system 700 is configured such that the first side 730 and the second side 732 can be joined and separated. For example, for insertion into the implantable medical device, the first side 730 and the second side 732 can be joined forming the guide system 700 and the conduit 708. Once the delivery system is inserted into the implantable medical device, the first side 730 and the second side 732 can be separated from removal from the delivery system.

Figure 7E:
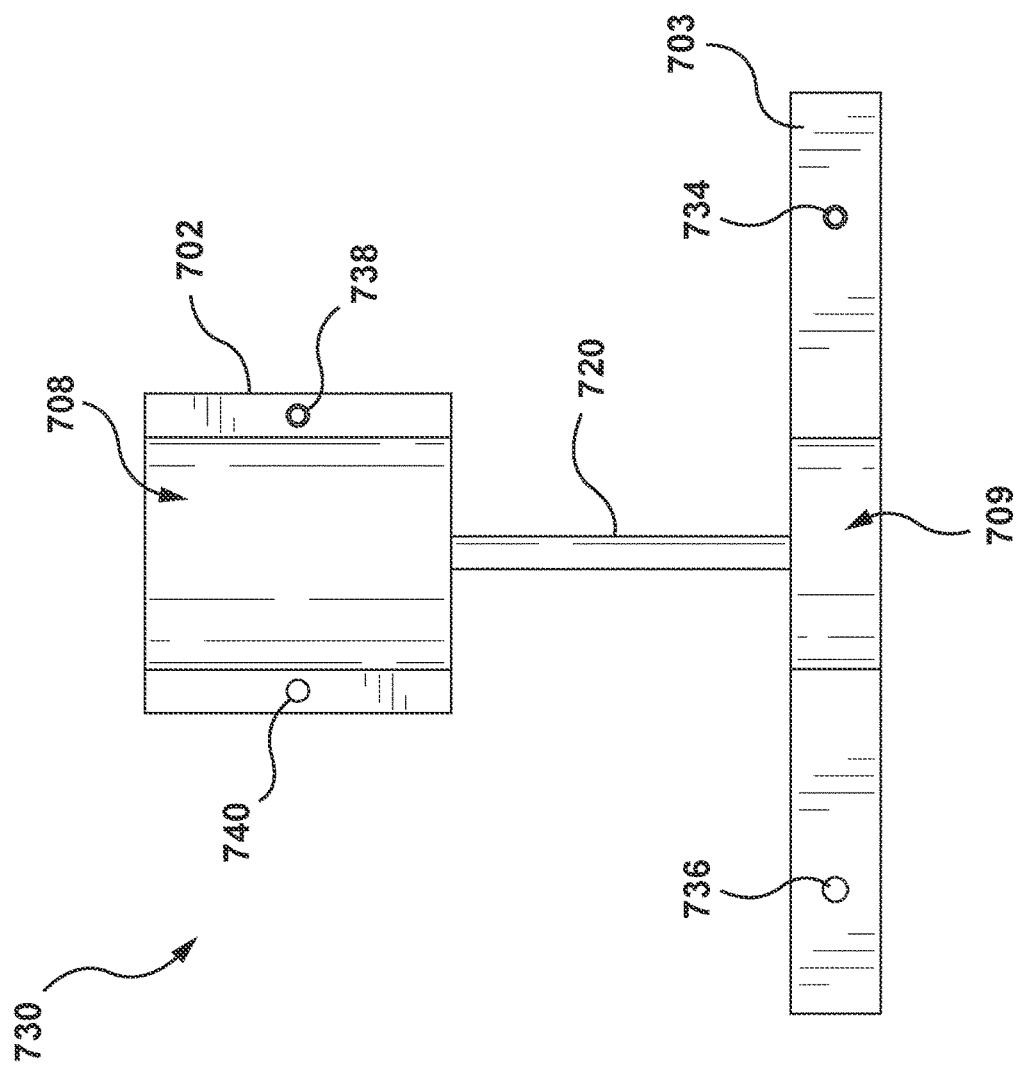
Figure 7F:
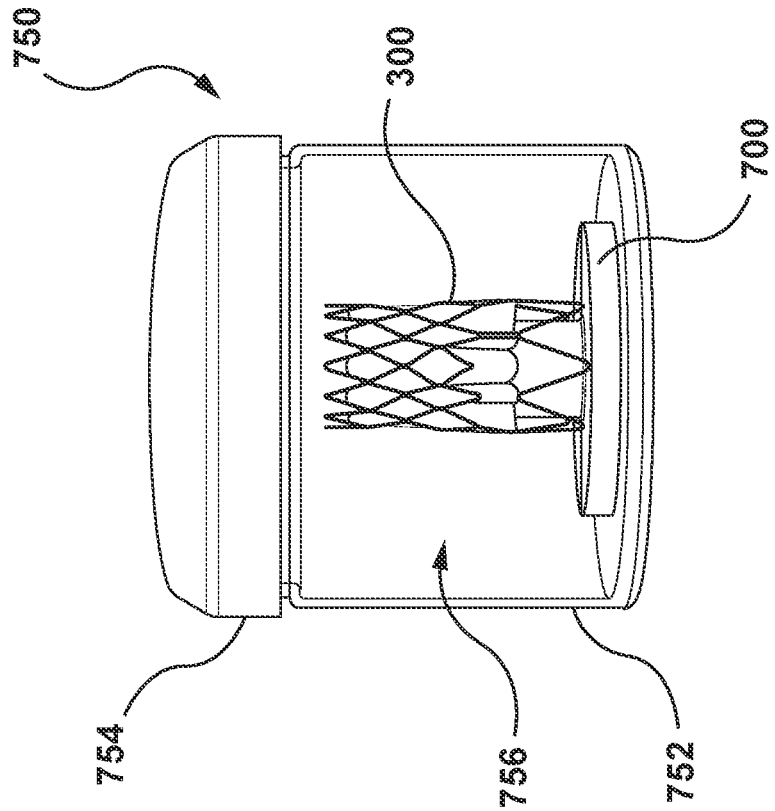
Figure 7G:
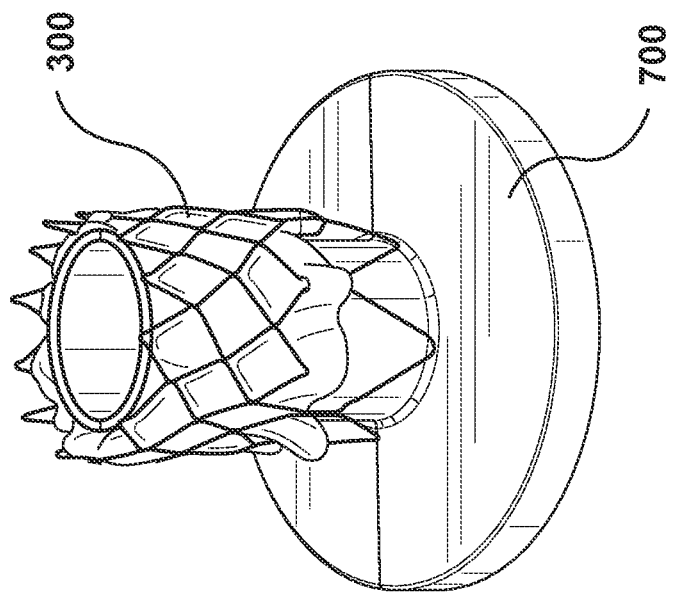
Figure 8:
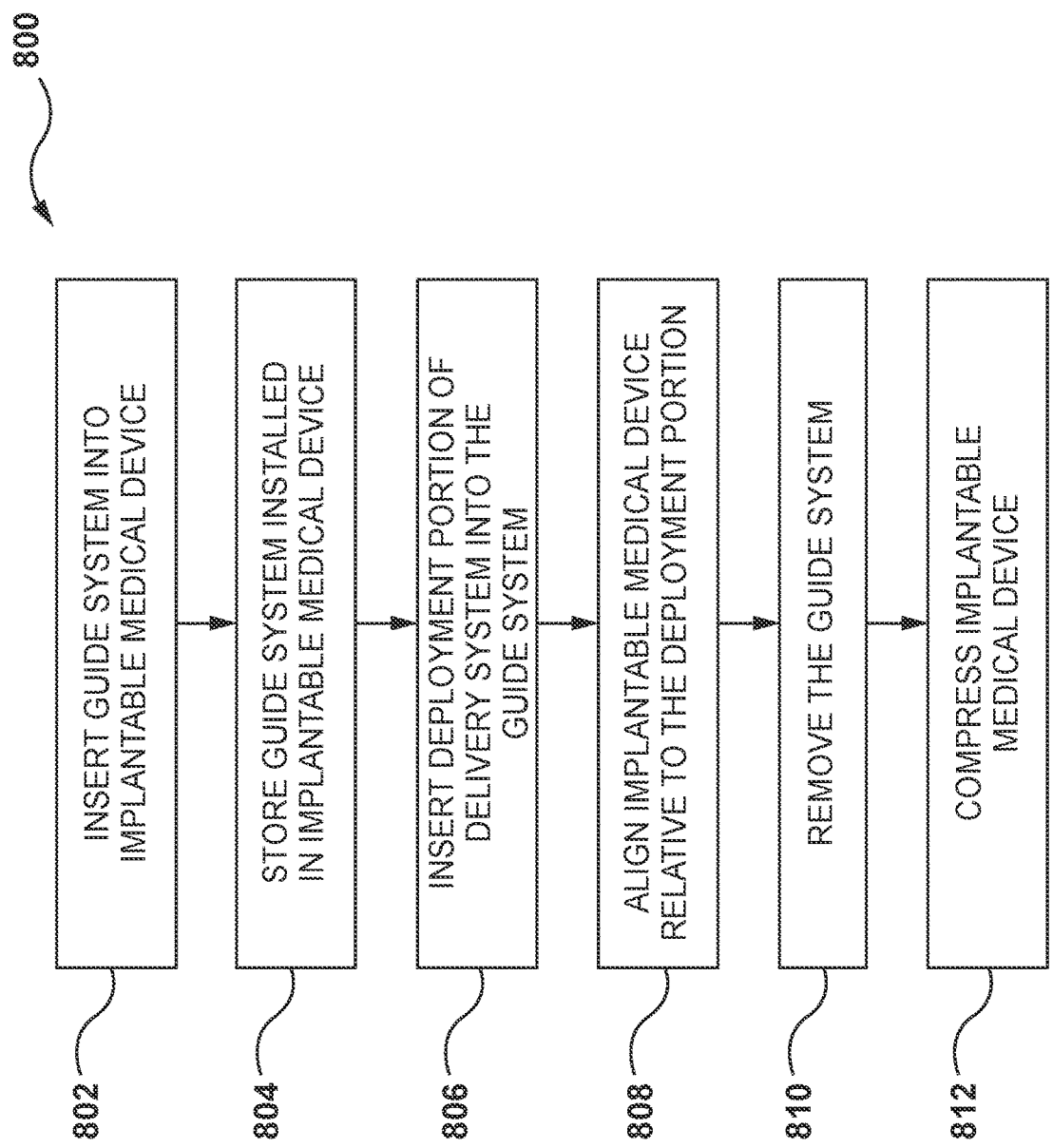

Each of the first side 730 and the second side 732 can include corresponding pins 734 and holes 736. For example, as illustrated in FIG. 7E, which is a side view of the first side 730, the first side 730 can include half of the body 702, half of the base 703, and one of the legs 720. The base 703 can include a pin 734 positioned on one side of the second end 709 of the conduit 708, and a hole positioned on the opposing side of the second end of the conduit 708. The pin 734 of the first side 730 engages with the hole 736 of the second side 732 when the first side 730 and second side 732 are joined. Likewise, the hole 736 of the first side 730 engage with the pin of the second side 732 when the first side 730 and the second side 732 are joined.

FIGS. 8, 9A-9C, and 10A-10C illustrate an example of a method 800 for loading an implantable medical device using the guide system 600 and/or 700, in accordance with an embodiment hereof. One skilled in the art will realize that FIGS. 8, 9A-9C, and 10A-10C illustrates one example of a method using the guide system 600 and/or 700 and that existing operations illustrated in FIG. 8 may be removed and/or additional operations may be added to the method 800.

In step 802, a guide system can be inserted into an implantable medical device. For example, as illustrated in FIG. 9A, the guide system 600 can be inserted into the prosthetic heart valve 200. In this example, the first end 604 of the guide system 600 can be inserted into the inflow end 212 of the prosthetic heart valve 200. The guide system 600 can be passed through the central lumen of the prosthetic heart valve 200 until the base 603 of the guide system 600 abuts the inflow end 212. As discussed above, the guide system 600 fits inside the central lumen of the prosthetic heart valve 200 to provide a conduit for inserting the delivery system 100 such that the guide system 600 protects the valve structure 204 and the stent 202 from damage by the delivery system 100. Additionally, as the guide system 600 is inserted through the prosthetic heart valve 200, the first end 604 of the guide system 600 applies a force on the leaflets 310 of the prosthetic heart valve 200. The force moves and directs the leaflets radially outward and towards the outflow end 214 of the prosthetic heart valve 200, thereby opening the leaflets.

In another example, as illustrated in FIG. 7F above, the first end 704 of the guide system 700 can be inserted into the outflow end 214 of the prosthetic heart valve 200. The body 702 operates to enter the central lumen of the prosthetic heart valve 200 and provide conduit for inserting delivery device. The base 703 operates as a stop to abut the outflow end 214 of the prosthetic heart valve 200 and prevent further insertion of the body 702. Once the body 702 is inserted into the central lumen of the prosthetic heart valve 200, the leaflets 206 of the prosthetic heart valve 200 can rest within the spaces 712 formed by the legs 720. As such, the leaflets 206 can rest in a closed state when the guide system 700 is inserted into the prosthetic heart valve 200.

For example, the prosthetic heart valve 200 may be installed on the guide system 700 such that the prosthetic heart valve 200 is propped up on guide system 700 with the legs 720 being aligned within commissure connections on the prosthetic heart valve 200. The length of the body 702 can be long enough so that the body 702 extends along the length of an inflow portion of the prosthetic heart valve 200. The configuration of the guide system 700 allows the guide system 700 to be packaged with the prosthetic heart valve 200 already mounted thereon. Further, the legs 720 can keep contact off the surfaces of the leaflets 206 to minimize abrasion and rubbing. Additionally, the legs 720 may serve to connect the body 702 and the base 703 together, thereby creating a mount or stand for the prosthetic heart valve 200.

In step 804, the guide system installed in the implantable medical device can be optionally stored. For example, as illustrated in FIG. 7G, the guide system 600 and/or 700 can be stored in a container such as a jar 750 that includes a body 750 and a lid 752 until the prosthetic heart valve 200 is ready to be loaded onto the delivery system 100.

In step 806, a distal portion of the delivery system is inserted into the guide system. For example, as illustrated in FIG. 9B, the distal portion 104 of the delivery system 100 can be inserted into the first end 604 of the guide system 600. The distal portion 104 can be advanced through the conduit 608 until the distal portion 104 protrudes from the second end 606 of the guide system 600. As the distal portion 104 of the delivery system 100 is inserted, the guide system 600 operates as a buffer between the distal portion 104 of the delivery system 100 and the implantable medical device. That is, because the guide fills the central lumen of the prosthetic heart valve 200 as the distal portion 104 is inserted, the distal portion 104 and other portions of the delivery system 100 only contact the inner surfaces of the guide systems and do not contact the prosthetic heart valve 200.

Figure 10A:
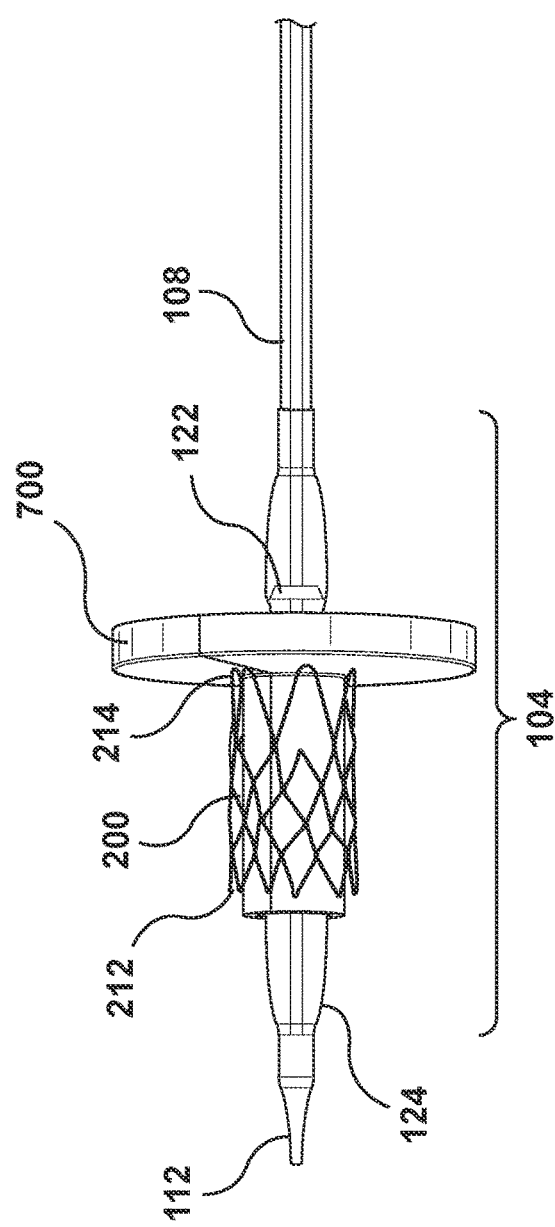
Figure 10B:
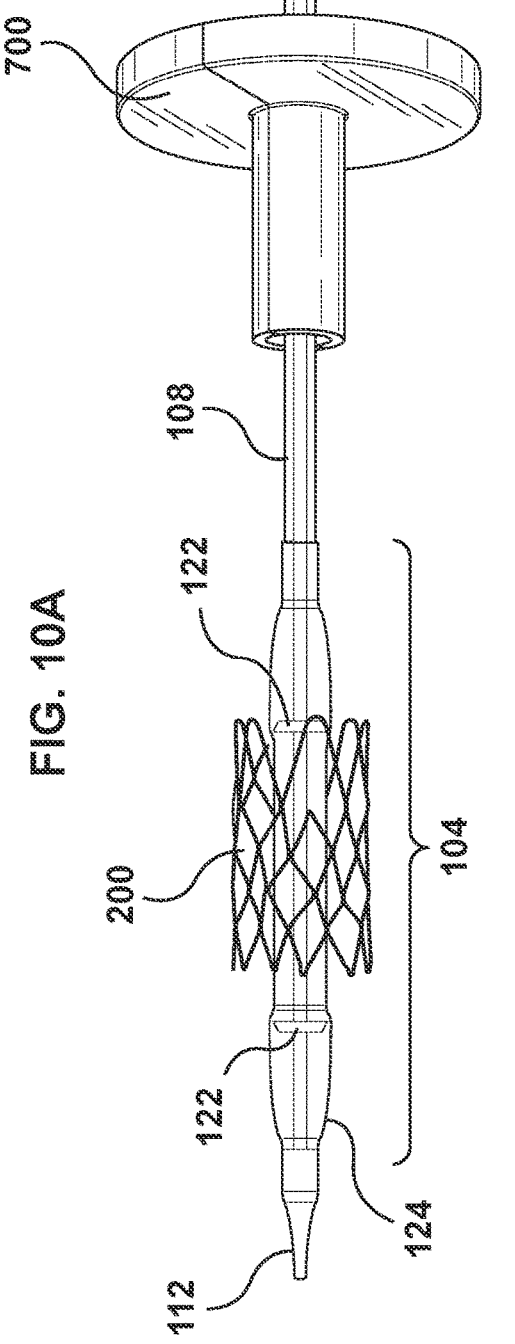
Figure 10C:
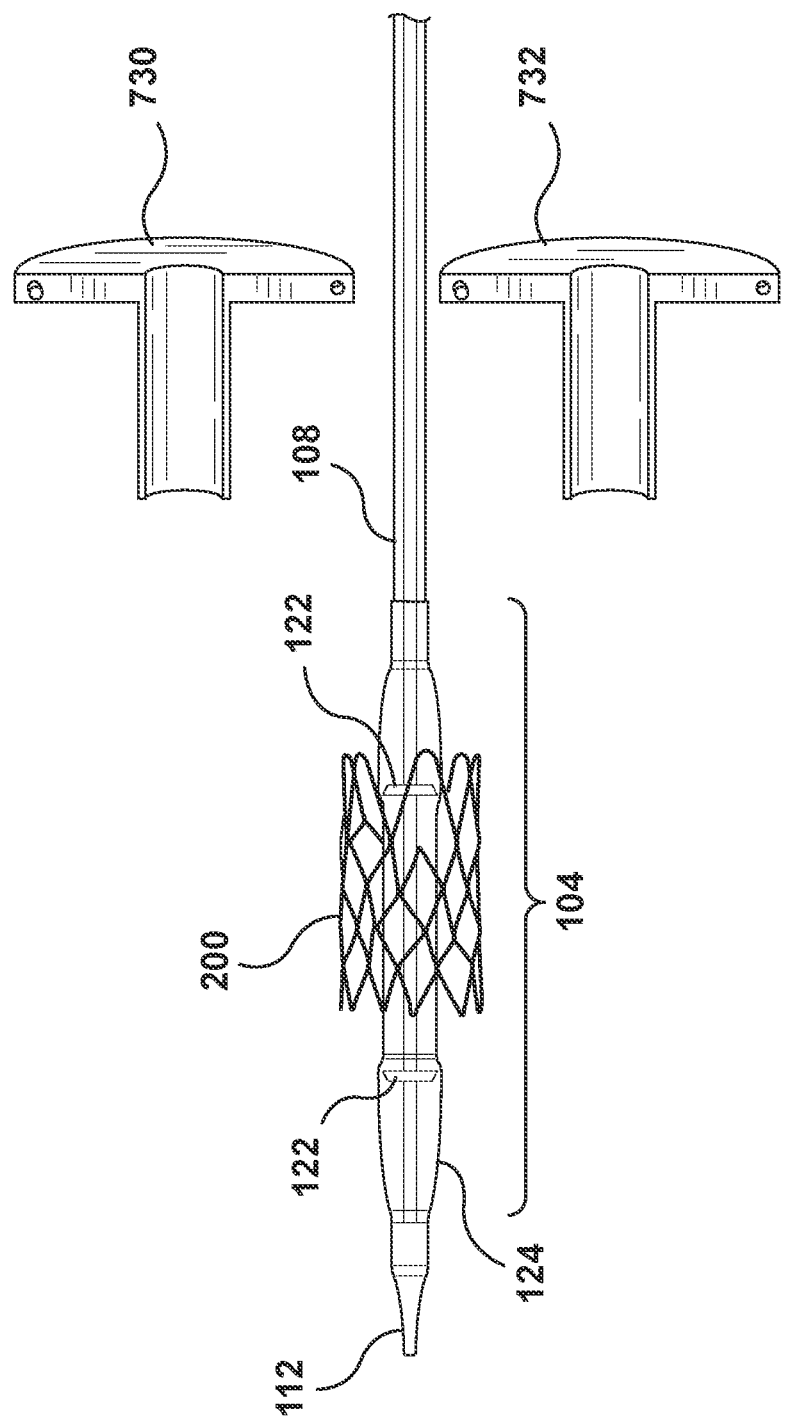

In another example illustrated in FIG. 10A-10C, the distal portion 104 of the delivery system 100 can be inserted into the second end 706 of the guide system 700. The distal portion 104 can be advanced through the conduit 708 until the distal portion 104 protrudes from the first end 704 of the guide system 700.

Figure 9C:
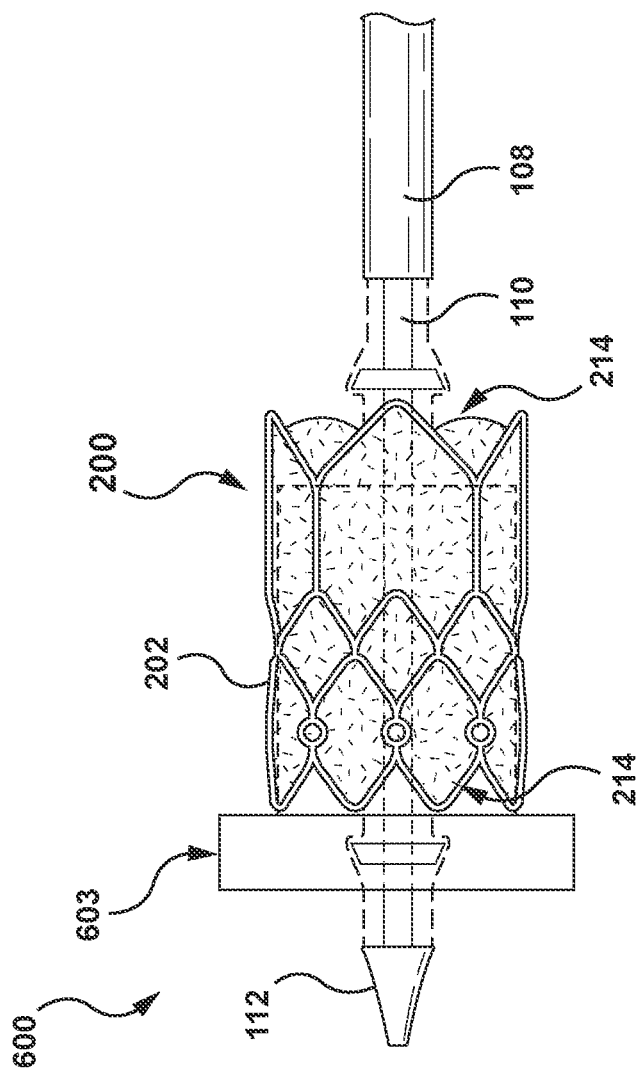

In step 808, the implantable medical device is aligned relative to the distal portion. For example, the distal portion 104 can be advanced for retracted within the conduit 608 and/or 708 until the prosthetic heart valve 200 is approximately aligned with the distal portion 104. For instance, the prosthetic heart valve 200 can be aligned so that it is between the retention member 222, as illustrated in FIG. 9C or FIG. 10A.

In step 810, the guide system is removed. In the example of FIGS. 9A-9C, the guide system 600 removed from the distal end of the catheter portion 102 once inserted into the conduit 608. In another example illustrated in FIGS. 10B and 10C, the guide system 700 can be advance further along the catheter portion 102 towards the proximal end of the catheter portion 202. Once the guide system 700 has been removed from the prosthetic heart valve 200, the guide system 700 can be divided into the first side 730 and second side 732 and removed from the catheter portion 102.

During loading onto a delivery system, the guide system 700 can operate to protect the prosthetic heart valve 200 from contact with the delivery system, for example, the distal portion 104 of the delivery system 100. Once the guide system 700 is retracted from the prosthetic heart valve 200, the guide system 700 can operate to move the leaflets 206 of the prosthetic heart valve 200 from a closed state to an open state. That is, as the guide system 700 is retracted from the outflow end 214 of the prosthetic heart valve 200, the body 704 can apply a force to the leaflets 206 to transition the leaflets 206 from the closed state to the open state.

For example, when a user aligns a delivery system for insertion into the guide system 700, the user may first pull the guide system 700 by the base 703 towards a proximal end of the prosthetic heart valve 200, thereby opening up the leaflets 206 on the prosthetic heart valve 200. As such, the delivery system then can be safely inserted through the opening at second end 706. Moreover, inserting the guide system 700 through an outflow portion of the prosthetic heart valve 200 may provide advantages. An amount of contact with the leaflets 206 contact is reduced, thereby reducing the friction due to contact. Additionally, this movement keeps the leaflets 206 in tension towards a proximal end and may not encourage inversion the leaflets 206.

In step 812, the implantable medical device can be compressed. For example, the prosthetic heart valve 200 aligned with the distal portion 104 can be inserted into a crimper chamber of a crimper. The crimper can be operated to compress the prosthetic heart valve 200 onto the distal portion 104.

It should be understood that various embodiments disclosed herein may be combined in different combinations than the combinations specifically presented in the description and accompanying drawings. It should also be understood that, depending on the example, certain acts or events of any of the processes or methods described herein may be performed in a different sequence, may be added, merged, or left out altogether (e.g., all described acts or events may not be necessary to carry out the techniques). In addition, while certain aspects of this disclosure are described as being performed by a single device or component for purposes of clarity, it should be understood that the techniques of this disclosure may be performed by a combination of devices or components associated with, for example, a medical device.

What is claimed is:

1. A system comprising:
   a delivery system including a proximal end and a distal end, the delivery system including an inner shaft and a balloon disposed over the inner shaft and a distal portion of the inner shaft;
   a prosthetic heart valve including a frame and a valve structure coupled to the frame, the prosthetic heart valve including an inflow end and an outflow end; and
   a guide system including a body comprising a first end, a second end, and a conduit extending from a first opening at the first end to a second opening at the second end, wherein:
      in a loading configuration, the body is disposed within the valve structure of the prosthetic heart valve and the balloon of the delivery system is disposed within the conduit of the body such that delivery system extends through the first opening and the second opening proximal and distal of the body, and
      in a delivery configuration, the guide system is removed from within the valve structure and the prosthetic heart valve is in a crimped state over the balloon.

2. The system of claim 1, wherein at least one of an outer diameter at the first end or an outer diameter at the second end is smaller than the outer diameter of the body.

3. The system of claim 1, wherein at least one of an inner diameter at the first end or an inner diameter at the second end is smaller than the inner diameter of the body.

4. The system of claim 1, wherein the inner diameter of the body varies along a long axis of the body.

5. The system of claim 4, wherein the variation of the inner diameter of the body comprises one or more steps in the inner diameter of the body.

6. The system of claim 4, wherein the variation of the inner diameter of the body comprises a continuous increase in the inner diameter of the body from the first end of the body to the second end of the body.

7. The system of claim 1, wherein the body further comprises:
   a plurality of perforations that enable the body to be divided into multiple portions such that in the delivery configuration the guide system is removed from the delivery system.

8. The system of claim 1, wherein the delivery system further includes a distal retention member disposed within the balloon, wherein in the delivery configuration, the distal retention member is distal of the prosthetic heart valve.

9. The system of claim 8, wherein the delivery system further includes a proximal retention member disposed within the balloon, wherein in the delivery configuration, the proximal retention member is proximal of the prosthetic valve.

10. The system of claim 9, wherein in the delivery configuration, the inflow end of the prosthetic heart valve is disposed adjacent the distal retention member and the outflow end of the prosthetic heart valve is disposed adjacent the proximal retention member.

11. The system of claim 1, wherein in the delivery configuration, the outflow end of the prosthetic heart valve is closer to the proximal end of the delivery system than the inflow end of the prosthetic heart valve is to the proximal end of the delivery system.

12. A method for loading a prosthetic heart valve onto a delivery system, the method comprising:
   inserting a guide system into a central lumen of the prosthetic heart valve, the guide system comprising a body that defines a conduit within an interior of the body;
   inserting a distal portion of the delivery system into the conduit of the guide system such that the delivery system extends proximal and distal of the guide system;
   aligning a distal retention member disposed within a balloon of the distal portion of the delivery system with the prosthetic heart valve such that the distal retention member is distal of the prosthetic heart valve;
   removing the guide system from the central lumen of the prosthetic heart valve; and
   compressing the prosthetic heart valve onto the distal portion of the delivery device.

13. The method of claim 12, wherein inserting the guide system comprises:
   inserting the guide system into an inflow end of the prosthetic heart valve and advancing the guide system towards the outflow end of the prosthetic heart valve.

14. The method of claim 12, wherein inserting a distal portion of the delivery system into the conduit of the guide system comprises inserting the distal portion into the conduit in a direction from the outflow end towards the inflow end of the prosthetic heart valve.

15. The method of claim 12, wherein the delivery system includes a proximal retention member, further comprising aligning the proximal retention member such that the proximal retention member is proximal of the prosthetic heart valve.

16. A method for loading a prosthetic heart valve onto a delivery system, the method comprising:
   inserting a guide system into a central lumen of the prosthetic heart valve, the guide system comprising a body that defines a conduit within an interior of the body;
   inserting a distal portion of the delivery system into the conduit of the guide system;
   aligning a distal retention member disposed within a balloon of the distal portion of the delivery system with the prosthetic heart valve such that the distal retention member is distal of the prosthetic heart valve;
   removing the guide system from the central lumen of the prosthetic heart valve by advancing the guide system proximally through the central lumen of the prosthetic heart valve over a catheter portion of the delivery system towards a handle of the delivery system; and
   compressing the prosthetic heart valve onto the distal portion of the delivery device.

17. The method of claim 16, the method further comprising:
   advancing the guide system over the prosthetic heart valve after compression of the prosthetic heart valve onto the distal portion of the delivery system to remove the guide system.

* * * * *